United States Patent
Terng et al.

(10) Patent No.: US 7,741,464 B2
(45) Date of Patent: Jun. 22, 2010

(54) COMPOSITIONS AND METHODS OF USING CRMP-1 AND ITS FRAGMENTS FOR TREATING CANCER

(75) Inventors: Harn-Jing Terng, Banciao (TW); Yi-Jen Lee, Keelung (TW); Woan-Jen Lee, Yonghe (TW)

(73) Assignee: Advpharma Inc., Taipei Hsien (TW)

( * ) Notice: Subject to any disclaimer, the term of this patent is extended or adjusted under 35 U.S.C. 154(b) by 0 days.

(21) Appl. No.: 12/076,722

(22) Filed: Mar. 21, 2008

(65) Prior Publication Data

US 2008/0287361 A1 Nov. 20, 2008

Related U.S. Application Data

(60) Provisional application No. 60/907,189, filed on Mar. 23, 2007.

(51) Int. Cl.
  *C07H 21/02* (2006.01)
(52) U.S. Cl. ..................................... 536/23.1
(58) Field of Classification Search ................. 536/23.1
  See application file for complete search history.

(56) References Cited

U.S. PATENT DOCUMENTS

| | | | |
|---|---|---|---|
| 6,046,173 A * | 4/2000 | Forstova et al. ............... | 514/44 |
| 7,354,709 B2 | 4/2008 | Yang et al. | |
| 2002/0168637 A1 | 11/2002 | Wang et al. | |
| 2003/0077624 A1* | 4/2003 | Yang et al. ..................... | 435/6 |

FOREIGN PATENT DOCUMENTS

| EP | 1 271 153 A | 1/2003 |
|---|---|---|
| EP | 1 271 153 A2 * | 1/2003 |
| WO | WO 2004/113566 A | 12/2004 |

OTHER PUBLICATIONS

Vivest et al (JBC, Jun. 1997, 272(25): 16010-16017).*
International Search Report from the European Patent Office, issued in International Application No. PCT/US2008/003724, dated Aug. 22, 2008 (8 pages), and Written Opinion of the International Searching Authority (10 pages).
Jin-Yuan Shih et al., "Collapsin Response Mediator Protein-1 and the Invasion and Metastasis of Cancer Cells", Journal of the National Cancer Institute, Service, 93:(18)1392-1400 (2001).
Jin-Yuan Shih et al., "Collapsin Response Mediator Protein-1: A novel invasion-suppressor gene", Clinical & Experimental Metastasis, 20:69-76 (2003).
Database UniProt:Q96I11_Human (1 page) (2001).
Database EMBL:CR601364 (2 pages) (2004).
Database EMBL:AL535253 (2 pages) (2001).
Database EMBL:CD579803 (2 pages) (2003).
Database EMBL:DA517748 (2 pages) (2005).
Albarran, et al., "A TAT-streptavidin fusion protein directs uptake of biotinylated cargo into mammalian cells", Protein Engineering, Design & Selection 18(3):147-152 (2005).
Byk et al., "Identification and molecular characterization of unc-33-like phosphoprotein (Ulip), a putative mammalian homology of the axonal guidance-associated unc-33 gene product", J. Neurosci. 16:688-701 (1996).
Chu, et al., "Selection of Invasive and Metastatic Subpopulations from a Human Lung Adenocarcinoma Cell Line", Am. J. Respir. Cell Mol. Biol., 17:353-360 (1997).
De Coupade, et al., "Novel human-derived cell-penetrating peptides for specific subcellular delivery of therapeutic biomolecules", Biochem. J. 390:407-418 (2005).
Harada, et al., "Antitumor Protein Therapy; Application of the Protein Transduction Domain to the Development of a Protein Drug for Cancer Treatment", Breast Cancer, 13(1)16-26 (2006).
Inagaki et al., "Differential expression of dihydropyrimidinase-related protein genes in developing and adult enteric nervous system", Histochem. Cell Biol., 113:37-41(2000).
Li et al., "Analysis of the *Caenohabditis elegans* Axonal Guidance and outgrowth Gene *unc-33*", Genetics, 132(3): 675-689 (1992).
Lin, et al., "Enhanced cell-permanent Cre protein for site-specific recombination in cultured cells", BMC Biotechnology, 4:25 (2004).
Lindsay, et al., "Peptide-mediated cell delivery: application in protein target validation", Pharmacology, 2:587-594 (2002).
Mamot, et al., "Epidermal Growth Factor Receptor (EGFR)-targeted Immunoliposomes Mediate Specific and Efficient Drug Delivery to EGFR- and EGFRvIII-overexpressing Tumor Cells", Cancer Research 63:3154-3161 (2003).
Matsuo et al., "Structure and promoter analysis of the human *unc-33*-like phosphoprotein gene: E-box required for maximal expression in neuroblastoma and myoblasts", *J. Biol. Chem.*, 275: 16560-16568 (2000).
Shih et al., "Collapsin Response Mediator Protein-1 and the Invasion and Metastasis of Cancer Cells", *J. Natl. Cancer Inst.*, 93(18): 1392-1400 (2001).
Shih et al., "Collapsin Response Mediator Protein-1: A Novel Invasion-Suppressor Gene", *Clinical & Exper. Metastasis*, 20: 69-76 (2003).
Torres and Polymeropoulos, "Genomic organization and localization of human CRMP-1 gene", DNA Res 5:393-395 (1998).
Vivés, et al., "A Truncated HIV-1 Tat Protein Basic Domain Rapidly Translocates through the Plasma Membrane and Accumulates in the Cell Nucleus", The Journal of Biological Chemistry, 272(25):16010-16017 (1997).

* cited by examiner

*Primary Examiner*—Sean E Aeder
(74) *Attorney, Agent, or Firm*—Hsiu-Ming Saunders Intellectual Property Connections, Inc.

(57) ABSTRACT

The present invention discloses a method for treating cancer by using hCRMP1 and/or active fragments thereof, as well as the active fragments of hCRMP1 that are capable of inhibiting cell proliferation, invasive activity, and metastasis of cancer. The method can also be used prior to, or in combination with, the administration a chemotherapy agent. A vector capable of expressing an hCRMP1, a variant of hCRMP1, a fragment of hCRMP1 or a variant of a fragment of hCRMP1 is also disclosed.

18 Claims, 18 Drawing Sheets

FIG. 1

SEQ ID NO: 1

MSYQGKKSIPHITSDRLLIKGGRIINDDQSLYADVYLEDGLIKQIGENLIVPGGVKTIEANG
RMVIPGGIDVNTYLQKPSQGMTAADDFFQGTRAALVGGTTMIIDHVVPEPGSSLLTSFE
KWHEAADTKSCCDYSLHVDITSWYDGVREELEVLVQDKGVNSFQVYMAYKDVYQMS
DSQLYEAFTFLKGLGAVILVHAENGDLIAQEQKRILEMGITGPEGHALSRPEELEAEAVF
RAITIAGRINCPVYITKVMSKSAADIIALARKKGPLVFGEPIAASLGTDGTHYWSKNWAK
AAAFVTSPPLSPDPTTPDYLTSLLACGDLQVTGSGHCPYSTAQKAVGKDNFTLIPEGVN
GIEERMTVVWDKAVATGKMDENQFVAVTSTNAAKIFNLYPRKGRIAVGSDADVVIWDPD
KLKTITAKSHKSAVEYNIFEGMECHGSPLVVISQGKIVFEDGNINVNKGMGRFIPRKAFP
EHLYQRVKIRNKVFGLQGVSRGMYDGPVYEVPATPKYATPAPSAKSSPSKHQPPPIRN
LHQSNFSLSGAQIDDNNPRRTGHRIVAPPGGRSNITSLG

FIG. 2A

SEQ ID NO: 2

5'-GTGGGCATCCACGGGCGCCGAGCCTCCGTCCGTGTCTCTATCCCTCCCGGGCC
TTTGTCAGCGCGCCCGCTGGGAGCGGGGCCGAGAGCGCCGGTTCCAGTCAGACA
GCCCCGCAGGTCAGCGGCCGGGCCGAGGGCGCCAGAGGGGGCCATGTCGTACC
AGGGCAAGAAGAGCATCCCGCACATCACGAGTGACCGACTCCTCATCAAAGGTGG
ACGGATCATCAACGATGACCAATCCCTTTATGCTGACGTCTACCTGGAGGATGGACT
TATCAAACAAATAGGAGAGAACTTAATCGTTCCTGGTGGAGTGAAGACCATTGAAGC
CAACGGGCGGATGGTTATTCCCGGAGGTATTGATGTCAACACGTACCTGCAGAAGC
CCTCCCAGGGGATGACTGCGGCTGATGACTTCTTCCAAGGGACCAGGGCGGCACT
GGTGGGCGGGACCACGATGATCATTGACCATGTTGTTCCTGAACCTGGGTCCAGC
CTACTGACCTCTTTCGAGAAGTGGCACGAAGCAGCTGACACCAAATCCTGCTGTGA
TTACTCCCTCCACGTGGACATCACAAGCTGGTACGATGGCGTTCGGGAGGAGCTG
GAGGTGCTGGTGCAGGACAAAGGCGTCAATTCCTTCCAAGTCTACATGGCCTATAA
GGATGTCTACCAAATGTCCGACAGCCAGCTCTATGAAGCCTTTACCTTCCTTAAGGG
CCTGGGAGCTGTGATCTTGGTCCATGCAGAAAATGGAGATTTGATAGCTCAGGAAC
AAAAGCGGATCCTGGAGATGGGCATCACGGGTCCCGAGGGCCATGCCCTGAGCA
GACCTGAAGAGCTGGAGGCCGAGGCGGTGTTCCGGGCCATCACCATTGCGGGCC
GGATCAACTGCCCTGTGTACATCACCAAGGTCATGAGCAAGAGTGCAGCCGACATC
ATCGCTCTGGCCAGGAAGAAAGGGCCCTAGTTTTTGGAGAGCCCATTGCCGCCA
GCCTGGGGACCGATGGCACCCATTACTGGAGCAAGAACTGGGCCAAGGCTGCGG
CGTTCGTGACTTCCCCTCCCCTGAGCCCGGACCCTACCACGCCCGACTACTTGAC
CTCCCTACTGGCCTGTGGGGACTTGCAGGTCACAGGCAGCGGCCACTGTCCCTAC
AGCACTGCCCAGAAGGCGGTGGGCAAGGACAACTTTACCCTGATCCCCGAGGGTG
TCAACGGGATAGAGGAGCGGATGACCGTCGTCTGGGACAAGGCGGTGGCTACTG
GCAAAATGGATGAGAACCAGTTTGTCGCTGTCACCAGCACCAATGCAGCCAAGATC
TTTAACCTGTACCCAAGGAAAGGGCGGATTGCCGTGGGCTCGGATGCCGACGTGG
TCATCTGGGACCCCGACAAGTTGAAGACCATAACAGCCAAAAGTCACAAGTCGGC

FIG. 2B

SEQ ID NO: 2 (continued)

GGTGGAGTACAACATCTTCGAGGGTATGGAGTGCCACGGCTCCCCACTAGTGGTCA
TCAGCCAGGGCAAGATCGTCTTTGAAGACGGAAACATCAACGTCAACAAGGGCAT
GGGCCGCTTCATTCCGCGGAAGGCGTTCCCGGAGCACCTGTACCAGCGCGTCAAA
ATCAGGAATAAGGTTTTTGGATTGCAAGGGGTTTCCAGGGGCATGTATGACGGTCC
TGTGTACGAGGTACCAGCTACACCCAAATATGCAACTCCCGCTCCTTCAGCCAAATC
TTCGCCTTCTAAACACCAGCCCCCACCCATCAGAAACCTCCACCAGTCCAACTTCA
GCTTATCAGGTGCCCAGATAGATGACAACAATCCCAGGCGCACCGGCCACCGCATC
GTGGCGCCCCTGGTGGCCGCTCCAACATCACCAGCCTCGGTTGAACGTGGATGC
GCGGAGGAGCTAGCCTGAAGGATTCTGGGAATCATGTCCATCCCTTTTCCTGTCAG
TGTTTTTGAAACCCACAGTTTTAGTTGGTGCTGATGGAGGGAGGGGGAAGTCGAAG
GATGCTCTTTCCCTTTTCTGTTTAGGAAGAAGTGGTACTAGTGTGGTGTGTTTGCTT
GGAAATTCCTTGCCCCACAGTTGTGTTCATGCTGAATCCACCTCGGAGCATGGTGT
TTTCATTCCCCCTTCCTAGTGAACCACAGGTTTTAGCATTGTCTTGTTCTGTCCCTTC
CACTTCTAACTCCACTGGCTCCATGATTCTCTGAGTGGTGGTTCCTTTGCACCCTGT
AGATGTTCTAGGATAGTTGATGCATGTTACTAAATTACGTATGCAAGTCTGTGAGTGC
GTCTGAGGGGACATCGCCAAGGACTGACTGAGACACGATGCCGAGACCTCAAGCC
CTGAGGGGCAGTCCCAAAACCCTTACAGTGAAGATGTTTACTCATTGCCCCCACCT
CTGGTCCACACTAGAAAGAAGCTCGCCCCACCTCCACCTGTGAGATCCGTGAATTC
TCGGAATGGCAGGGGAAGCCTTGCACTAGGTTGCAGAGAAGCATCCTCCACATCC
TGTGTCAGAAACCCTGGTCTCCGTGGCACTTGTAACTCACCGTGCTGTCTTCTGGT
CTGTGTGTGTTCTTCAAGCCAGCTCTAGGCTTCAGGCCGAGCCAGGTTCACACTCA
GAAAGATGTCTCCCCATCCCCATTCGGGGCTGACGATGGGGGGCTGATGGCTGCC
CCTGCGTGGCCTGAGTCCTGGTCCCTCTGAGGCAGTTGACGGGGCAGTCAGATTT
TTAAAGTTTTGTACAAAGTTTTCCTTTGTAATCACTCCCATTTTTACTTAACAACCAAC
TTGTTGTGGCTCTTATTTCTGAATTCAAAGCTTGTGAAAAAATAAAAGAAAATGAACT
GCCC-3'

FIG. 3

SEQ ID NO: 3

5'-GATTCTCGAGGGGGCCATGTCGTACCAGGGCAAG-3'

FIG. 4

SEQ ID NO: 4

5'-GTCTAGATCAGTGATGGTGGTGGTGATGACCGAGGCTGGTGATG-3'

FIG. 5

SEQ ID NO: 5

5'-ACTCGAGGCCATGTCGTACCAGGGCAAGAAG-3'

FIG. 6

SEQ ID NO: 6

5'-CTCGAGACCATGGAACAAAAGCGGATCCTGG-3'

FIG. 7

SEQ ID NO: 7

5'-CTCGAGACCATGGACTACTTGACCTCCCTAC-3'

FIG. 8

SEQ ID NO: 8

5'-TTCTAGACTACTGGTACAGGTGCTCCGGG-3'

FIG. 9

SEQ ID NO: 9

5'-GAATACTCATACTCTTCCGGATCCGTCGACGCCACC
ATGGTGCTGGTGCAGGACAAAGG-3'

FIG. 10

SEQ ID NO: 10

5'-GAATACTCATACTCTTCCGGATCCGTCGACGCCACC
ATGATAGCTCAGGAACAAAAG-3'

FIG. 11

SEQ ID NO: 11

5'-GAATACTCATACTCTTCCGGATCCGTCGACGCCACC
ATGAACATCAACGTCAACAAGG-3'

FIG. 12

SEQ ID NO: 12

5'-CAGCGGCCGCTCAGTGGTGGTGATGGTGGTGGTCGGCTGCACTCTTGCTC-3'

FIG. 13

SEQ ID NO: 13

5'-TAGCGGCCGCTCAGTGATGATGGTGATGATGTAGGGAGGTCAAGTAGTCG-3'

FIG. 14

SEQ ID NO: 14

5'-TAGCGGCCGCTCAGTGATGATGGTGATGATGACCGAGGCTGGTGATGTTGG-3'

FIG. 15

SEQ ID NO: 15

MSYQGKKSIPHITSDRLLIKGGRIINDDQSLYADVYLEDGLIKQIGENLIVPGGVKTIEANG
RMVIPGGIDVNTYLQKPSQGMTAADDFFQGTRAALVGGTTMIIDHVVPEPGSSLLTSFE
KWHEAADTKSCCDYSLHVDITSWYDGVREELEVLVQDKGVNSFQVYMAYKDVYQMS
DSQLYEAFTFLKGLGAVILVHAENGDLIAQEQKRILEMGITGPEGHALSRPEELEAEAVF
RAITIAGRINCPVYITKVMSKSAADIIALARKKGPLVFGEPIAASLGTDGTHYWSKNWAK
AAAFVTSPPLSPDPTTPDYLTSLLACGDLQVTGSGHCPYSTAQKAVGKDNFTLIPEGVN
GIEERMTVVWDKAVATGKMDENQFVAVTSTNAAKIFNLYPRKGRIAVGSDADVVIWDPD
KLKTITAKSHKSAVEYNIFEGMECHGSPLVVISQGKIVFEDGNINVNKGMGRFIPRKAFP
EHLYQ

FIG. 16

SEQ ID NO: 16

5'-ACTCGAGGCCATGTCGTACCAGGGCAAGAAGAGCATCCCGCACATCACGAGTG
ACCGACTCCTCATCAAAGGTGGACGGATCATCAACGATGACCAATCCCTTTATGCTG
ACGTCTACCTGGAGGATGGACTTATCAAACAAATAGGAGAGAACTTAATCGTTCCTG
GTGGAGTGAAGACCATTGAAGCCAACGGGCGGATGGTTATTCCCGGAGGTATTGAT
GTCAACACGTACCTGCAGAAGCCCTCCCAGGGGATGACTGCGGCTGATGACTTCT
TCCAAGGGACCAGGGCGGCACTGGTGGGCGGGACCACGATGATCATTGACCATGT
TGTTCCTGAACCTGGGTCCAGCCTACTGACCTCTTTCGAGAAGTGGCACGAAGCA
GCTGACACCAAATCCTGCTGTGATTACTCCCTCCACGTGGACATCACAAGCTGGTA
CGATGGCGTTCGGGAGGAGCTGGAGGTGCTGGTGCAGGACAAAGGCGTCAATTC
CTTCCAAGTCTACATGGCCTATAAGGATGTCTACCAAATGTCCGACAGCCAGCTCTA
TGAAGCCTTTACCTTCCTTAAGGGCCTGGGAGCTGTGATCTTGGTCCATGCAGAAA
ATGGAGATTTGATAGCTCAGGAACAAAAGCGGATCCTGGAGATGGGCATCACGGGT
CCCGAGGGCCATGCCCTGAGCAGACCTGAAGAGCTGGAGGCCGAGGCGGTGTTC
CGGGCCATCACCATTGCGGGCCGGATCAACTGCCCTGTGTACATCACCAAGGTCAT
GAGCAAGAGTGCAGCCGACATCATCGCTCTGGCCAGGAAGAAAGGGCCCCTAGTT
TTTGGAGAGCCCATTGCCGCCAGCCTGGGGACCGATGGCACCCATTACTGGAGCA
AGAACTGGGCCAAGGCTGCGGCGTTCGTGACTTCCCCTCCCCTGAGCCCGGACC
CTACCACGCCCGACTACTTGACCTCCCTACTGGCCTGTGGGGACTTGCAGGTCAC
AGGCAGCGGCCACTGTCCCTACAGCACTGCCCAGAAGGCGGTGGGCAAGGACAA
CTTTACCCTGATCCCCGAGGGTGTCAACGGGATAGAGGAGCGGATGACGGTCGTC
TGGGACAAGGCGGTGGCTACTGGCAAAATGGATGAGAACCAGTTTGTCGCTGTCA
CCAGCACCAATGCAGCCAAGATCTTTAACCTGTACCCAAGGAAAGGGCGGATTGCC
GTGGGCTCGGATGCCGACGTGGTCATCTGGGACCCCGACAAGTTGAAGACCATAA
CAGCCAAAAGTCACAAGTCGGCGGTGGAGTACAACATCTTCGAGGGTATGGAGTG
CCACGGCTCCCCACTAGTGGTCATCAGCCAGGGCAAGATCGTCTTTGAAGACGGA
AACATCAACGTCAACAAGGGCATGGGCCGCTTCATTCCGCGGAAGGCGTTCCCGG
AGCACCTGTACCAGTAGTCTAGAA-3'

FIG. 17A

SEQ ID NO: 17

MEQKRILEMGITGPEGHALSRPEELEAEAVFRAITIAGRINCPVYITKVMSKSAADIIALA
RKKGPLVFGEPIAASLGTDGTHYWSKNWAKAAAFVTSPPLSPDPTTPDYLTSLLACGD
LQVTGSGHCPYSTAQKAVGKDNFTLIPEGVNGIEERMTVVWDKAVATGKMDENQFVAV
TSTNAAKIFNLYPRKGRIAVGSDADVVIWDPDKLKTITAKSHKSAVEYNIFEGMECHGSP
LVVISQGKIVFEDGNINVNKGMGRFIPRKAFPEHLYQ

FIG. 17B

SEQ ID NO: 39

EQKRILEMGITGPEGHALSRPEELEAEAVFRAITIAGRINCPVYITKVMSKSAADIIALARK
KGPLVFGEPIAASLGTDGTHYWSKNWAKAAAFVTSPPLSPDPTTPDYLTSLLACGDLQ
VTGSGHCPYSTAQKAVGKDNFTLIPEGVNGIEERMTVVWDKAVATGKMDENQFVAVTS
TNAAKIFNLYPRKGRIAVGSDADVVIWDPDKLKTITAKSHKSAVEYNIFEGMECHGSPLV
VISQGKIVFEDGNINVNKGMGRFIPRKAFPEHLYQ

FIG. 18

SEQ ID NO: 18

5'-CTCGAGACCATGGAACAAAAGCGGATCCTGGAGATGGGCATCACGGGTCCCGA
GGGCCATGCCCTGAGCAGACCTGAAGAGCTGGAGGCCGAGGCGGTGTTCCGGGC
CATCACCATTGCGGGCCGGATCAACTGCCCTGTGTACATCACCAAGGTCATGAGCA
AGAGTGCAGCCGACATCATCGCTCTGGCCAGGAAGAAAGGGCCCCTAGTTTTTGG
AGAGCCCATTGCCGCCAGCCTGGGGACCGATGGCACCCATTACTGGAGCAAGAAC
TGGGCCAAGGCTGCGGCGTTCGTGACTTCCCCTCCCCTGAGCCCGGACCCTACCA
CGCCCGACTACTTGACCTCCCTACTGGCCTGTGGGGACTTGCAGGTCACAGGCAG
CGGCCACTGTCCCTACAGCACTGCCCAGAAGGCGGTGGGCAAGGACAACTTTACC
CTGATCCCCGAGGGTGTCAACGGGATAGAGGAGCGGATGACGGTCGTCTGGGACA
AGGCGGTGGCTACTGGCAAAATGGATGAGAACCAGTTTGTCGCTGTCACCAGCAC
CAATGCAGCCAAGATCTTTAACCTGTACCCAAGGAAAGGGCGGATTGCCGTGGGCT
CGGATGCCGACGTGGTCATCTGGGACCCCGACAAGTTGAAGACCATAACAGCCAA
AAGTCACAAGTCGGCGGTGGAGTACAACATCTTCGAGGGTATGGAGTGCCACGGC
TCCCCACTAGTGGTCATCAGCCAGGGCAAGATCGTCTTTGAAGACGGAAACATCAA
CGTCAACAAGGGCATGGGCCGCTTCATTCCGCGGAAGGCGTTCCCGGAGCACCT
GTACCAGTAGTCTAGAA-3'

FIG. 19A

SEQ ID NO: 19

MDYLTSLLACGDLQVTGSGHCPYSTAQKAVGKDNFTLIPEGVNGIEERMTVVWDKAVA
TGKMDENQFVAVTSTNAAKIFNLYPRKGRIAVGSDADVVIWDPDKLKTITAKSHKSAVEY
NIFEGMECHGSPLVVISQGKIVFEDGNINVNKGMGRFIPRKAFPEHLYQ

FIG. 19B

SEQ ID NO: 40

DYLTSLLACGDLQVTGSGHCPYSTAQKAVGKDNFTLIPEGVNGIEERMTVVWDKAVAT
GKMDENQFVAVTSTNAAKIFNLYPRKGRIAVGSDADVVIWDPDKLKTITAKSHKSAVEY
NIFEGMECHGSPLVVISQGKIVFEDGNINVNKGMGRFIPRKAFPEHLYQ

FIG. 20

SEQ ID NO: 20

5'-CTCGAGACCATGGACTACTTGACCTCCCTACTGGCCTGTGGGGACTTGCAGGT
CACAGGCAGCGGCCACTGTCCCTACAGCACTGCCCAGAAGGCGGTGGGCAAGGA
CAACTTTACCCTGATCCCCGAGGGTGTCAACGGGATAGAGGAGCGGATGACGGTC
GTCTGGGACAAGGCGGTGGCTACTGGCAAAATGGATGAGAACCAGTTTGTCGCTG
TCACCAGCACCAATGCAGCCAAGATCTTTAACCTGTACCCAAGGAAAGGGCGGATT
GCCGTGGGCTCGGATGCCGACGTGGTCATCTGGGACCCCGACAAGTTGAAGACCA
TAACAGCCAAAAGTCACAAGTCGGCGGTGGAGTACAACATCTTCGAGGGTATGGAG
TGCCACGGCTCCCCACTAGTGGTCATCAGCCAGGGCAAGATCGTCTTTGAAGACG
GAAACATCAACGTCAACAAGGGCATGGGCCGCTTCATTCCGCGGAAGGCGTTCCC
GGAGCACCTGTACCAGTAGTCTAGAA-3'

FIG. 21A

SEQ ID NO: 21

MVLVQDKGVNSFQVYMAYKDVYQMSDSQLYEAFTFLKGLGAVILVHAENGDLIAQEQK
RILEMGITGPEGHALSRPEELEAEAVFRAITIAGRINCPVYITKVMSKSAADHHHHHH

FIG. 21B

SEQ ID NO: 41

VLVQDKGVNSFQVYMAYKDVYQMSDSQLYEAFTFLKGLGAVILVHAENGDLIAQEQKRI
LEMGITGPEGHALSRPEELEAEAVFRAITIAGRINCPVYITKVMSKSAAD

FIG. 22

SEQ ID NO: 22

5'-GAATACTCATACTCTTCCGGATCCGTCGACGCCACCATGGTGCTGGTGCAGGAC
AAAGGCGTCAATTCCTTCCAAGTCTACATGGCCTATAAGGATGTCTACCAAATGTCC
GACAGCCAGCTCTATGAAGCCTTTACCTTCCTTAAGGGCCTGGGAGCTGTGATCTT
GGTCCATGCAGAAAATGGAGATTTGATAGCTCAGGAACAAAAGCGGATCCTGGAGA
TGGGCATCACGGGTCCCGAGGGCCATGCCCTGAGCAGACCTGAAGAGCTGGAGG
CCGAGGCGGTGTTCCGGGCCATCACCATTGCGGGCCGGATCAACTGCCCTGTGTA
CATCACCAAGGTCATGAGCAAGAGTGCAGCCGACCACCACCATCACCACCACTGA
GCGGCCGCTG-3'

FIG. 23A

SEQ ID NO: 23

MIAQEQKRILEMGITGPEGHALSRPEELEAEAVFRAITIAGRINCPVYITKVMSKSAADIIA
LARKKGPLVFGEPIAASLGTDGTHYWSKNWAKAAAFVTSPPLSPDPTTPDYLTSLHHH
HHH

FIG. 23B

SEQ ID NO: 42

IAQEQKRILEMGITGPEGHALSRPEELEAEAVFRAITIAGRINCPVYITKVMSKSAADIIAL
ARKKGPLVFGEPIAASLGTDGTHYWSKNWAKAAAFVTSPPLSPDPTTPDYLTSL

FIG. 24

SEQ ID NO: 24

5'-GAATACTCATACTCTTCCGGATCCGTCGACGCCACCATGATAGCTCAGGAACAAA
AGCGGATCCTGGAGATGGGCATCACGGGTCCCGAGGGCCATGCCCTGAGCAGAC
CTGAAGAGCTGGAGGCCGAGGCGGTGTTCCGGGCCATCACCATTGCGGGCCGGA
TCAACTGCCCTGTGTACATCACCAAGGTCATGAGCAAGAGTGCAGCCGACATCATC
GCTCTGGCCAGGAAGAAAGGGCCCCTAGTTTTTGGAGAGCCCATTGCCGCCAGCC
TGGGGACCGATGGCACCCATTACTGGAGCAAGAACTGGGCCAAGGCTGCGGCGTT
CGTGACTTCCCCTCCCTGAGCCCGGACCCTACCACGCCCGACTACTTGACCTCC
CTACATCATCACCATCATCACTGAGCGGCCGCTA-3'

FIG. 25A

SEQ ID NO: 25

MNINVNKGMGRFIPRKAFPEHLYQRVKIRNKVFGLQGVSRGMYDGPVYEVPATPKYAT
PAPSAKSSPSKHQPPPIRNLHQSNFSLSGAQIDDNNPRRTGHRIVAPPGGRSNITSLGH
HHHHH

FIG. 25B

SEQ ID NO: 43

NINVNKGMGRFIPRKAFPEHLYQRVKIRNKVFGLQGVSRGMYDGPVYEVPATPKYATP
APSAKSSPSKHQPPPIRNLHQSNFSLSGAQIDDNNPRRTGHRIVAPPGGRSNITSLG

FIG. 26

SEQ ID NO: 26

5'-GAATACTCATACTCTTCCGGATCCGTCGACGCCACCATGAACATCAACGTCAACA
AGGGCATGGGCCGCTTCATTCCGCGGAAGGCGTTCCCGGAGCACCTGTACCAGC
GCGTCAAAATCAGGAATAAGGTTTTTGGATTGCAAGGGGTTTCCAGGGGCATGTAT
GACGGTCCTGTGTACGAGGTACCAGCTACACCCAAATATGCAACTCCCGCTCCTTC
AGCCAAATCTTCGCCTTCTAAACACCAGCCCCCACCCATCAGAAACCTCCACCAGT
CCAACTTCAGCTTATCAGGTGCCCAGATAGATGACAACAATCCCAGGCGCACCGGC
CACCGCATCGTGGCGCCCCCTGGTGGCCGCTCCAACATCACCAGCCTCGGTCATC
ATCACCATCATCACTGAGCGGCCGCTA-3'

FIG. 27

SEQ ID NO: 27

5'-ATTGAAAGCTTATGTCGTACCAGGGCA-3'

FIG. 28

SEQ ID NO: 28

5'-ATATCCTCGAGACCGAGGCTGGTGATG-3'

FIG. 29

SEQ ID NO: 29

5'-AGCAAGCTTGAACAAAAGCGGATCCTG-3'

FIG. 30

SEQ ID NO: 30

5'-TAACTCGAGCTGGTACAGGTGCTCC-3'

FIG. 31

SEQ ID NO: 31

5' - TATGTACGGTCGTAAAAAACGTCGTCAGCGTCGTCGG - 3'

FIG. 32

SEQ ID NO: 32

5'- GATCCCGACGACGCTGACGACGTTTTTTACGACCGTACA - 3'

FIG. 33

SEQ ID NO: 33

5'-ATGTCGTACCAGGGCAAGAAGAGCATCCCGCACATCACGAGTGACCGACTCCTC
ATCAAAGGTGGACGGATCATCAACGATGACCAATCCCTTTATGCTGACGTCTACCTG
GAGGATGGACTTATCAAACAAATAGGAGAGAACTTAATCGTTCCTGGTGGAGTGAA
GACCATTGAAGCCAACGGGCGGATGGTTATTCCCGGAGGTATTGATGTCAACACGT
ACCTGCAGAAGCCCTCCCAGGGGATGACTGCGGCTGATGACTTCTTCCAAGGGAC
CAGGGCGGCACTGGTGGGCGGGACCACGATGATCATTGACCATGTTGTTCCTGAA
CCTGGGTCCAGCCTACTGACCTCTTTCGAGAAGTGGCACGAAGCAGCTGACACCA
AATCCTGCTGTGATTACTCCCTCCACGTGGACATCACAAGCTGGTACGATGGCGTT
CGGGAGGAGCTGGAGGTGCTGGTGCAGGACAAAGGCGTCAATTCCTTCCAAGTCT
ACATGGCCTATAAGGATGTCTACCAAATGTCCGACAGCCAGCTCTATGAAGCCTTTA
CCTTCCTTAAGGGCCTGGGAGCTGTGATCTTGGTCCATGCAGAAAATGGAGATTTG
ATAGCTCAGGAACAAAAGCGGATCCTGGAGATGGGCATCACGGGTCCCGAGGGCC
ATGCCCTGAGCAGACCTGAAGAGCTGGAGGCCGAGGCGGTGTTCCGGGCCATCA
CCATTGCGGGCCGGATCAACTGCCCTGTGTACATCACCAAGGTCATGAGCAAGAGT
GCAGCCGACATCATCGCTCTGGCCAGGAAGAAAGGGCCCCTAGTTTTTGGAGAGC
CCATTGCCGCCAGCCTGGGGACCGATGGCACCCATTACTGGAGCAAGAACTGGGC
CAAGGCTGCGGCGTTCGTGACTTCCCCTCCCCTGAGCCCGGACCCTACCACGCCC
GACTACTTGACCTCCCTACTGGCCTGTGGGGACTTGCAGGTCACAGGCAGCGGCC
ACTGTCCCTACAGCACTGCCCAGAAGGCGGTGGGCAAGGACAACTTTACCCTGAT
CCCCGAGGGTGTCAACGGGATAGAGGAGCGGATGACGGTCGTCTGGGACAAGGC
GGTGGCTACTGGCAAAATGGATGAGAACCAGTTTGTCGCTGTCACCAGCACCAATG
CAGCCAAGATCTTTAACCTGTACCCAAGGAAAGGGCGGATTGCCGTGGGCTCGGA
TGCCGACGTGGTCATCTGGGACCCCGACAAGTTGAAGACCATAACAGCCAAAGT
CACAAGTCGGCGGTGGAGTACAACATCTTCGAGGGTATGGAGTGCCACGGCTCCC
CACTAGTGGTCATCAGCCAGGGCAAGATCGTCTTTGAAGACGGAAACATCAACGTC
AACAAGGGCATGGGCCGCTTCATTCCGCGGAAGGCGTTCCCGGAGCACCTGTACC
AG-3'

FIG. 34

SEQ ID NO: 34

5'-GAACAAAAGCGGATCCTGGAGATGGGCATCACGGGTCCCGAGGGCCATGCCCT
GAGCAGACCTGAAGAGCTGGAGGCCGAGGCGGTGTTCCGGGCCATCACCATTGC
GGGCCGGATCAACTGCCCTGTGTACATCACCAAGGTCATGAGCAAGAGTGCAGCC
GACATCATCGCTCTGGCCAGGAAGAAAGGGCCCCTAGTTTTTGGAGAGCCCATTGC
CGCCAGCCTGGGGACCGATGGCACCCATTACTGGAGCAAGAACTGGGCCAAGGC
TGCGGCGTTCGTGACTTCCCCTCCCCTGAGCCCGGACCCTACCACGCCCGACTAC
TTGACCTCCCTACTGGCCTGTGGGGACTTGCAGGTCACAGGCAGCGGCCACTGTC
CCTACAGCACTGCCCAGAAGGCGGTGGGCAAGGACAACTTTACCCTGATCCCCGA
GGGTGTCAACGGGATAGAGGAGCGGATGACGGTCGTCTGGGACAAGGCGGTGGC
TACTGGCAAAATGGATGAGAACCAGTTTGTCGCTGTCACCAGCACCAATGCAGCCA
AGATCTTTAACCTGTACCCAAGGAAAGGGCGGATTGCCGTGGGCTCGGATGCCGA
CGTGGTCATCTGGGACCCCGACAAGTTGAAGACCATAACAGCCAAAAGTCACAAGT
CGGCGGTGGAGTACAACATCTTCGAGGGTATGGAGTGCCACGGCTCCCCACTAGT
GGTCATCAGCCAGGGCAAGATCGTCTTTGAAGACGGAAACATCAACGTCAACAAG
GGCATGGGCCGCTTCATTCCGCGGAAGGCGTTCCCGGAGCACCTGTACCAG-3'

FIG. 35

SEQ ID NO: 35

5'-GACTACTTGACCTCCCTACTGGCCTGTGGGGACTTGCAGGTCACAGGCAGCGG
CCACTGTCCCTACAGCACTGCCCAGAAGGCGGTGGGCAAGGACAACTTTACCCTG
ATCCCCGAGGGTGTCAACGGGATAGAGGAGCGGATGACGGTCGTCTGGGACAAG
GCGGTGGCTACTGGCAAAATGGATGAGAACCAGTTTGTCGCTGTCACCAGCACCAA
TGCAGCCAAGATCTTTAACCTGTACCCAAGGAAAGGGCGGATTGCCGTGGGCTCG
GATGCCGACGTGGTCATCTGGGACCCCGACAAGTTGAAGACCATAACAGCCAAAA
GTCACAAGTCGGCGGTGGAGTACAACATCTTCGAGGGTATGGAGTGCCACGGCTC
CCCACTAGTGGTCATCAGCCAGGGCAAGATCGTCTTTGAAGACGGAAACATCAACG
TCAACAAGGGCATGGGCCGCTTCATTCCGCGGAAGGCGTTCCCGGAGCACCTGTA
CCAG-3'

FIG. 36

SEQ ID NO: 36

5'-GTGCTGGTGCAGGACAAAGGCGTCAATTCCTTCCAAGTCTACATGGCCTATAAG
GATGTCTACCAAATGTCCGACAGCCAGCTCTATGAAGCCTTTACCTTCCTTAAGGGC
CTGGGAGCTGTGATCTTGGTCCATGCAGAAAATGGAGATTTGATAGCTCAGGAACA
AAAGCGGATCCTGGAGATGGGCATCACGGGTCCCGAGGGCCATGCCCTGAGCAG
ACCTGAAGAGCTGGAGGCCGAGGCGGTGTTCCGGGCCATCACCATTGCGGGCCG
GATCAACTGCCCTGTGTACATCACCAAGGTCATGAGCAAGAGTGCAGCCGAC-3'

FIG. 37

SEQ ID NO: 37

5'-ATAGCTCAGGAACAAAAGCGGATCCTGGAGATGGGCATCACGGGTCCCGAGGG
CCATGCCCTGAGCAGACCTGAAGAGCTGGAGGCCGAGGCGGTGTTCCGGGCCAT
CACCATTGCGGGCCGGATCAACTGCCCTGTGTACATCACCAAGGTCATGAGCAAGA
GTGCAGCCGACATCATCGCTCTGGCCAGGAAGAAAGGGCCCCTAGTTTTTGGAGA
GCCCATTGCCGCCAGCCTGGGGACCGATGGCACCCATTACTGGAGCAAGAACTGG
GCCAAGGCTGCGGCGTTCGTGACTTCCCCTCCCCTGAGCCCGGACCCTACCACG
CCCGACTACTTGACCTCCCTA-3'

FIG. 38

SEQ ID NO: 38

5'-AACATCAACGTCAACAAGGGCATGGGCCGCTTCATTCCGCGGAAGGCGTTCCC
GGAGCACCTGTACCAGCGCGTCAAAATCAGGAATAAGGTTTTTGGATTGCAAGGGG
TTTCCAGGGGCATGTATGACGGTCCTGTGTACGAGGTACCAGCTACACCCAAATATG
CAACTCCCGCTCCTTCAGCCAAATCTTCGCCTTCTAAACACCAGCCCCCACCCATC
AGAAACCTCCACCAGTCCAACTTCAGCTTATCAGGTGCCCAGATAGATGACAACAAT
CCCAGGCGCACCGGCCACCGCATCGTGGCGCCCCTGGTGGCCGCTCCAACATC
ACCAGCCTCGGT-3'

SEQUENCE LISTING

<160> NUMBER OF SEQ ID NOS: 45

<210> SEQ ID NO 1
<211> LENGTH: 572
<212> TYPE: PRT
<213> ORGANISM: Homo sapiens

<400> SEQUENCE: 1

```
Met Ser Tyr Gln Gly Lys Lys Ser Ile Pro His Ile Thr Ser Asp Arg
 1               5                   10                  15

Leu Leu Ile Lys Gly Gly Arg Ile Ile Asn Asp Asp Gln Ser Leu Tyr
            20                  25                  30

Ala Asp Val Tyr Leu Glu Asp Gly Leu Ile Lys Gln Ile Gly Glu Asn
        35                  40                  45

Leu Ile Val Pro Gly Gly Val Lys Thr Ile Glu Ala Asn Gly Arg Met
    50                  55                  60

Val Ile Pro Gly Gly Ile Asp Val Asn Thr Tyr Leu Gln Lys Pro Ser
 65                  70                  75                  80

Gln Gly Met Thr Ala Ala Asp Asp Phe Phe Gln Gly Thr Arg Ala Ala
                85                  90                  95

Leu Val Gly Gly Thr Thr Met Ile Ile Asp His Val Val Pro Glu Pro
            100                 105                 110

Gly Ser Ser Leu Leu Thr Ser Phe Glu Lys Trp His Glu Ala Ala Asp
        115                 120                 125

Thr Lys Ser Cys Cys Asp Tyr Ser Leu His Val Asp Ile Thr Ser Trp
    130                 135                 140

Tyr Asp Gly Val Arg Glu Glu Leu Glu Val Leu Val Gln Asp Lys Gly
145                 150                 155                 160

Val Asn Ser Phe Gln Val Tyr Met Ala Tyr Lys Asp Val Tyr Gln Met
                165                 170                 175

Ser Asp Ser Gln Leu Tyr Glu Ala Phe Thr Phe Leu Lys Gly Leu Gly
            180                 185                 190

Ala Val Ile Leu Val His Ala Glu Asn Gly Asp Leu Ile Ala Gln Glu
        195                 200                 205

Gln Lys Arg Ile Leu Glu Met Gly Ile Thr Gly Pro Glu Gly His Ala
    210                 215                 220

Leu Ser Arg Pro Glu Glu Leu Glu Ala Glu Ala Val Phe Arg Ala Ile
225                 230                 235                 240
```

| | | | | | | | | | | | |
|---|---|---|---|---|---|---|---|---|---|---|---|
|Thr|Ile|Ala|Gly|Arg|Ile|Asn|Cys|Pro|Val|Tyr|Ile|Thr|Lys|Val|Met|
| | | |245| | | |250| | | |255| | | | |

Ser Lys Ser Ala Ala Asp Ile Ile Ala Leu Ala Arg Lys Lys Gly Pro
           260             265             270

Leu Val Phe Gly Glu Pro Ile Ala Ala Ser Leu Gly Thr Asp Gly Thr
               275             280             285

His Tyr Trp Ser Lys Asn Trp Ala Lys Ala Ala Phe Val Thr Ser
       290             295             300

Pro Pro Leu Ser Pro Asp Pro Thr Thr Pro Asp Tyr Leu Thr Ser Leu
305             310             315             320

Leu Ala Cys Gly Asp Leu Gln Val Thr Gly Ser His Cys Pro Tyr
               325             330             335

Ser Thr Ala Gln Lys Ala Val Gly Lys Asp Asn Phe Thr Leu Ile Pro
           340             345             350

Glu Gly Val Asn Gly Ile Glu Glu Arg Met Thr Val Val Trp Asp Lys
           355             360             365

Ala Val Ala Thr Gly Lys Met Asp Glu Asn Gln Phe Val Ala Val Thr
       370             375             380

Ser Thr Asn Ala Ala Lys Ile Phe Asn Leu Tyr Pro Arg Lys Gly Arg
385             390             395             400

Ile Ala Val Gly Ser Asp Ala Asp Val Val Ile Trp Asp Pro Asp Lys
               405             410             415

Leu Lys Thr Ile Thr Ala Lys Ser His Lys Ser Ala Val Glu Tyr Asn
           420             425             430

Ile Phe Glu Gly Met Glu Cys His Gly Ser Pro Leu Val Val Ile Ser
           435             440             445

Gln Gly Lys Ile Val Phe Glu Asp Gly Asn Ile Asn Val Asn Lys Gly
       450             455             460

Met Gly Arg Phe Ile Pro Arg Lys Ala Phe Pro Glu His Leu Tyr Gln
465             470             475             480

Arg Val Lys Ile Arg Asn Lys Val Phe Gly Leu Gln Gly Val Ser Arg
               485             490             495

Gly Met Tyr Asp Gly Pro Val Tyr Glu Val Pro Ala Thr Pro Lys Tyr
           500             505             510

Ala Thr Pro Ala Pro Ser Ala Lys Ser Ser Pro Ser Lys His Gln Pro
           515             520             525

Pro Pro Ile Arg Asn Leu His Gln Ser Asn Phe Ser Leu Ser Gly Ala
       530             535             540

Gln Ile Asp Asp Asn Asn Pro Arg Arg Thr Gly His Arg Ile Val Ala
545             550             555             560

Pro Pro Gly Gly Arg Ser Asn Ile Thr Ser Leu Gly
               565             570

<210> SEQ ID NO 2
<211> LENGTH: 2842
<212> TYPE: DNA
<213> ORGANISM: Homo sapiens

<400> SEQUENCE: 2

```
gtgggcatcc acgggcgccg agcctccgtc cgtgtctcta tccctcccgg gcctttgtca    60
gcgcgcccgc tgggagcggg gccgagagcg ccggttccag tcagacagcc ccgcaggtca   120
gcggccgggc cgagggcgcc agaggggggc atgtcgtacc agggcaagaa gagcatcccg   180
cacatcacga gtgaccgact cctcatcaaa ggtggacgga tcatcaacga tgaccaatcc   240
```

-continued

```
ctttatgctg acgtctacct ggaggatgga cttatcaaac aaataggaga gaacttaatc    300
gttcctggtg gagtgaagac cattgaagcc aacgggcgga tggttattcc cggaggtatt    360
gatgtcaaca cgtacctgca gaagccctcc caggggatga ctgcggctga tgacttcttc    420
caagggacca gggcggcact ggtgggcggg accacgatga tcattgacca tgttgttcct    480
gaacctgggt ccagcctact gacctctttc gagaagtggc acgaagcagc tgacaccaaa    540
tcctgctgtg attactccct ccacgtggac atcacaagct ggtacgatgg cgttcgggag    600
gagctggagg tgctggtgca ggacaaaggc gtcaattcct tccaagtcta catggcctat    660
aaggatgtct accaaatgtc cgacagccag ctctatgaag cctttacctt ccttaagggc    720
ctgggagctg tgatcttggt ccatgcagaa aatggagatt tgatagctca ggaacaaaag    780
cggatcctgg agatgggcat cacgggtccc gagggccatg ccctgagcag acctgaagag    840
ctggaggccg aggcggtgtt ccgggccatc accattgcgg gccggatcaa ctgccctgtg    900
tacatcacca aggtcatgag caagagtgca gccgacatca tcgctctggc caggaagaaa    960
gggccgctag ttttttggaga gcccattgcc gccagcctgg ggaccgatgg cacccattac   1020
tggagcaaga actgggccaa ggctgcggcg ttcgtgactt cccctcccct gagcccggac   1080
cctaccacgc ccgactactt gacctcccta ctggcctgtg gggacttgca ggtcacaggc   1140
agcggccact gtccctacag cactgcccag aaggcggtgg gcaaggacaa ctttacccctg  1200
atccccgagg gtgtcaacgg gatagaggag cggatgaccg tcgtctggga caaggcggtg   1260
gctactggca aaatggatga gaaccagttt gtcgctgtca ccagcaccaa tgcagccaag   1320
atctttaacc tgtacccaag gaaagggcgg attgccgtgg gctcggatgc cgacgtggtc   1380
atctgggacc ccgacaagtt gaagaccata acagccaaaa gtcacaagtc ggcggtggag   1440
tacaacatct tcgagggtat ggagtgccac ggctccccac tagtggtcat cagccagggc   1500
aagatcgtct ttgaagacgg aaacatcaac gtcaacaagg gcatgggccg cttcattccg   1560
cggaaggcgt tcccggagca cctgtaccag cgcgtcaaaa tcaggaataa ggttttttgga  1620
ttgcaagggg tttccagggg catgtatgac ggtcctgtgt acgaggtacc agctacaccc   1680
aaatatgcaa ctcccgctcc ttcagccaaa tcttcgcctt ctaaacacca gccccccaccc  1740
atcagaaacc tccaccagtc caacttcagc ttatcaggtg cccagataga tgacaacaat   1800
cccaggcgca ccggccaccg catcgtggcg cccccctggtg gccgctccaa catcaccagc  1860
ctcggttgaa cgtggatgcg cggaggagct agcctgaagg attctgggaa tcatgtccat   1920
ccctttttcct gtcagtgttt ttgaaaccca cagttttagt tggtgctgat ggagggaggg  1980
ggaagtcgaa ggatgctctt tccctttttct gtttaggaag aagtggtact agtgtggtgt   2040
gtttgcttgg aaattccttg ccccacagtt gtgttcatgc tgaatccacc tcggagcatg   2100
gtgttttcat tccccctttcc tagtgaacca caggttttag cattgtcttg ttctgtccct   2160
tccacttcta actccactgg ctccatgatt ctctgagtgg tggttccttt gcaccctgta   2220
gatgttctag gatagttgat gcatgttact aaattacgta tgcaagtctg tgagtgcgtc   2280
tgaggggaca tcgccaagga ctgactgaga cacgatgccg agacctcaag ccctgagggg   2340
cagtcccaaa acccttacag tgaagatgtt tactcattgc ccccacctct ggtccacact   2400
agaaagaagc tcgccccacc tccacctgtg agatccgtga attctcggaa tggcagggga   2460
agccttgcac taggttgcag agaagcatcc tccacatcct gtgtcagaaa ccctggtctc   2520
cgtggcactt gtaactcacc gtgctgtctt ctggtctgtg tgtgttcttc aagccagctc   2580
taggcttcag gccgagccag gttcacactc agaaagatgt ctccccatcc ccattcgggg   2640
```

-continued

```
ctgacgatgg ggggctgatg gctgccctg cgtggcctga gtcctggtcc ctctgaggca    2700
gttgacgggg cagtcagatt tttaaagttt tgtacaaagt tttcctttgt aatcactccc    2760 attttactt aacaaccaac ttgttgtggc tcttatttct gaattcaaag cttgtgaaaa    2820
aataaaagaa aatgaactgc cc                                              2842
```

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

```
gattctcgag ggggccatgt cgtaccaggg caag                                 34
```

<210> SEQ ID NO 4
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

```
gtctagatca gtgatggtgg tggtgatgac cgaggctggt gatg                      44
```

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

```
actcgaggcc atgtcgtacc agggcaagaa g                                    31
```

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
ctcgagacca tggaacaaaa gcggatcctg g                                    31
```

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

```
ctcgagacca tggactactt gacctcccta c                                    31
```

<210> SEQ ID NO 8
<211> LENGTH: 29
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 8
ttctagacta ctggtacagg tgctccggg                                        29

<210> SEQ ID NO 9
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gaatactcat actcttccgg atccgtcgac gccaccatgg tgctggtgca ggacaaagg      59

<210> SEQ ID NO 10
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gaatactcat actcttccgg atccgtcgac gccaccatga tagctcagga acaaaag        57

<210> SEQ ID NO 11
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gaatactcat actcttccgg atccgtcgac gccaccatga acatcaacgt caacaagg       58

<210> SEQ ID NO 12
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cagcggccgc tcagtggtgg tgatggtggt ggtcggctgc actcttgctc                50

<210> SEQ ID NO 13
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tagcggccgc tcagtgatga tggtgatgat gtagggaggt caagtagtcg                50

<210> SEQ ID NO 14
<211> LENGTH: 51
<212> TYPE: DNA
<213> ORGANISM: Artificial Sequence
<220> FEATURE:
```

-continued

<223> OTHER INFORMATION: Description of Artificial Sequence: Synthetic primer

<400> SEQUENCE: 14
tagcggccgc tcagtgatga tggtgatgat gaccgaggct ggtgatgttg g           51

<210> SEQ ID NO 15
<211> LENGTH: 480
<212> TYPE: PRT
<213> ORGANISM: Homo sapiens

<400> SEQUENCE: 15

```
Met Ser Tyr Gln Gly Lys Lys Ser Ile Pro His Ile Thr Ser Asp Arg
 1               5                  10                  15

Leu Leu Ile Lys Gly Gly Arg Ile Ile Asn Asp Asp Gln Ser Leu Tyr
            20                  25                  30

Ala Asp Val Tyr Leu Glu Asp Gly Leu Ile Lys Gln Ile Gly Glu Asn
        35                  40                  45

Leu Ile Val Pro Gly Gly Val Lys Thr Ile Glu Ala Asn Gly Arg Met
    50                  55                  60

Val Ile Pro Gly Gly Ile Asp Val Asn Thr Tyr Leu Gln Lys Pro Ser
65                  70                  75                  80

Gln Gly Met Thr Ala Ala Asp Asp Phe Phe Gln Gly Thr Arg Ala Ala
                85                  90                  95

Leu Val Gly Gly Thr Thr Met Ile Ile Asp His Val Val Pro Glu Pro
           100                 105                 110

Gly Ser Ser Leu Leu Thr Ser Phe Glu Lys Trp His Glu Ala Ala Asp
       115                 120                 125

Thr Lys Ser Cys Cys Asp Tyr Ser Leu His Val Asp Ile Thr Ser Trp
   130                 135                 140

Tyr Asp Gly Val Arg Glu Glu Leu Glu Val Leu Val Gln Asp Lys Gly
145                 150                 155                 160

Val Asn Ser Phe Gln Val Tyr Met Ala Tyr Lys Asp Val Tyr Gln Met
                165                 170                 175

Ser Asp Ser Gln Leu Tyr Glu Ala Phe Thr Phe Leu Lys Gly Leu Gly
            180                 185                 190

Ala Val Ile Leu Val His Ala Glu Asn Gly Asp Leu Ile Ala Gln Glu
        195                 200                 205

Gln Lys Arg Ile Leu Glu Met Gly Ile Thr Gly Pro Glu Gly His Ala
    210                 215                 220

Leu Ser Arg Pro Glu Glu Leu Glu Ala Glu Ala Val Phe Arg Ala Ile
225                 230                 235                 240

Thr Ile Ala Gly Arg Ile Asn Cys Pro Val Tyr Ile Thr Lys Val Met
                245                 250                 255

Ser Lys Ser Ala Ala Asp Ile Ile Ala Leu Ala Arg Lys Lys Gly Pro
            260                 265                 270

Leu Val Phe Gly Glu Pro Ile Ala Ala Ser Leu Gly Thr Asp Gly Thr
        275                 280                 285

His Tyr Trp Ser Lys Asn Trp Ala Lys Ala Ala Phe Val Thr Ser
    290                 295                 300

Pro Pro Leu Ser Pro Asp Pro Thr Thr Pro Asp Tyr Leu Thr Ser Leu
305                 310                 315                 320

Leu Ala Cys Gly Asp Leu Gln Val Thr Gly Ser Gly His Cys Pro Tyr
                325                 330                 335

Ser Thr Ala Gln Lys Ala Val Gly Lys Asp Asn Phe Thr Leu Ile Pro
```

|  | 340 |  |  | 345 |  |  |  | 350 |  |  |
|---|---|---|---|---|---|---|---|---|---|---|

Glu Gly Val Asn Gly Ile Glu Arg Met Thr Val Val Trp Asp Lys
        355                 360                 365

Ala Val Ala Thr Gly Lys Met Asp Glu Asn Gln Phe Val Ala Val Thr
        370                 375                 380

Ser Thr Asn Ala Ala Lys Ile Phe Asn Leu Tyr Pro Arg Lys Gly Arg
385                 390                 395                 400

Ile Ala Val Gly Ser Asp Ala Asp Val Val Ile Trp Asp Pro Asp Lys
                405                 410                 415

Leu Lys Thr Ile Thr Ala Lys Ser His Lys Ser Ala Val Glu Tyr Asn
        420                 425                 430

Ile Phe Glu Gly Met Glu Cys His Gly Ser Pro Leu Val Val Ile Ser
        435                 440                 445

Gln Gly Lys Ile Val Phe Glu Asp Gly Asn Ile Asn Val Asn Lys Gly
        450                 455                 460

Met Gly Arg Phe Ile Pro Arg Lys Ala Phe Pro Glu His Leu Tyr Gln
465                 470                 475                 480

<210> SEQ ID NO 16
<211> LENGTH: 1460
<212> TYPE: DNA
<213> ORGANISM: Homo sapiens

<400> SEQUENCE: 16

```
actcgaggcc atgtcgtacc agggcaagaa gagcatcccg cacatcacga gtgaccgact    60
cctcatcaaa ggtggacgga tcatcaacga tgaccaatcc ctttatgctg acgtctacct   120
ggaggatgga cttatcaaac aaataggaga aacttaatc gttcctggtg gagtgaagac    180
cattgaagcc aacgggcgga tggttattcc cggaggtatt gatgtcaaca cgtacctgca   240
gaagccctcc caggggatga ctgcggctga tgacttcttc aagggaccag ggcggcact    300
ggtgggcggg accacgatga tcattgacca tgttgttcct gaacctgggt ccagcctact   360
gacctctttc gagaagtggc acgaagcagc tgacaccaaa tcctgctgtg attactccct   420
ccacgtggac atcacaagct ggtacgatgg cgttcgggag gagctggagg tgctggtgca   480
ggacaaaggc gtcaattcct tccaagtcta catggcctat aaggatgtct accaaatgtc   540
cgacagccag ctctatgaag cctttacctt ccttaagggc ctgggagctg tgatcttggt   600
ccatgcagaa aatggagatt tgatagctca ggaacaaaag cggatcctgg agatgggcat   660
cacgggtccc gagggccatg ccctgagcag acctgaagag ctggaggccg aggcggtgtt   720
ccggccatc accattgcgg gccggatcaa ctgccctgtg tacatcacca aggtcatgag   780
caagagtgca gccgacatca tcgctctggc caggaagaaa gggcccctag ttttggaga    840
gcccattgcc gccagcctgg ggaccgatgg cacccattac tggagcaaga actgggccaa   900
ggctgcggcg ttcgtgactt cccctcccct gagcccggac cctaccacgc ccgactactt   960
gacctcccta ctggcctgtg ggacttgca ggtcacaggc agcggccact gtccctacag   1020
cactgcccag aaggcggtgg gcaaggacaa ctttaccctg atccccgagg tgtcaacgg   1080
gatagaggag cggatgacgg tcgtctggga caaggcggtg gctactggca aaatggatga   1140
gaaccagttt gtcgctgtca ccagcaccaa tgcagccaag atctttaacc tgtacccaag   1200
gaaagggcgg attgccgtgg gctcggatgc cgacgtggtc atctgggacc ccgacaagtt   1260
gaagaccata acagccaaaa gtcacaagtc ggcggtggag tacaacatct tcgagggtat   1320
ggagtgccac ggctccccac tagtggtcat cagccagggc aagatcgtct ttgaagacgg   1380
```
aaacatcaac gtcaacaagg gcatgggccg cttcattccg cggaaggcgt tcccggagca    1440
cctgtaccag tagtctagaa                                                1460

<210> SEQ ID NO 17
<211> LENGTH: 274
<212> TYPE: PRT
<213> ORGANISM: Homo sapiens

<400> SEQUENCE: 17

```
Met Glu Gln Lys Arg Ile Leu Glu Met Gly Ile Thr Gly Pro Glu Gly
 1               5                  10                  15
His Ala Leu Ser Arg Pro Glu Leu Glu Ala Glu Ala Val Phe Arg
            20                  25                  30
Ala Ile Thr Ile Ala Gly Arg Ile Asn Cys Pro Val Tyr Ile Thr Lys
        35                  40                  45
Val Met Ser Lys Ser Ala Ala Asp Ile Ile Ala Leu Ala Arg Lys Lys
    50                  55                  60
Gly Pro Leu Val Phe Gly Glu Pro Ile Ala Ala Ser Leu Gly Thr Asp
65                  70                  75                  80
Gly Thr His Tyr Trp Ser Lys Asn Trp Ala Lys Ala Ala Phe Val
                85                  90                  95
Thr Ser Pro Pro Leu Ser Pro Asp Pro Thr Thr Pro Asp Tyr Leu Thr
            100                 105                 110
Ser Leu Leu Ala Cys Gly Asp Leu Gln Val Thr Gly Ser Gly His Cys
        115                 120                 125
Pro Tyr Ser Thr Ala Gln Lys Ala Val Gly Lys Asp Asn Phe Thr Leu
    130                 135                 140
Ile Pro Glu Gly Val Asn Gly Ile Glu Glu Arg Met Thr Val Val Trp
145                 150                 155                 160
Asp Lys Ala Val Ala Thr Gly Lys Met Asp Glu Asn Gln Phe Val Ala
                165                 170                 175
Val Thr Ser Thr Asn Ala Ala Lys Ile Phe Asn Leu Tyr Pro Arg Lys
            180                 185                 190
Gly Arg Ile Ala Val Gly Ser Asp Ala Asp Val Val Ile Trp Asp Pro
        195                 200                 205
Asp Lys Leu Lys Thr Ile Thr Ala Lys Ser His Lys Ser Ala Val Glu
    210                 215                 220
Tyr Asn Ile Phe Glu Gly Met Glu Cys His Gly Ser Pro Leu Val Val
225                 230                 235                 240
Ile Ser Gln Gly Lys Ile Val Phe Glu Asp Gly Asn Ile Asn Val Asn
                245                 250                 255
Lys Gly Met Gly Arg Phe Ile Pro Arg Lys Ala Phe Pro Glu His Leu
            260                 265                 270
Tyr Gln
```

<210> SEQ ID NO 18
<211> LENGTH: 841
<212> TYPE: DNA
<213> ORGANISM: Homo sapiens

<400> SEQUENCE: 18
ctcgagacca tggaacaaaa gcggatcctg gagatgggca tcacgggtcc cgagggccat    60
gccctgagca gacctgaaga gctggaggcc gaggcggtgt tccgggccat caccattgcg   120
ggccggatca actgccctgt gtacatcacc aaggtcatga gcaagagtgc agccgacatc   180

```
atcgctctgg ccaggaagaa agggccccta gttttggag agcccattgc cgccagcctg    240
gggaccgatg caccatta ctggagcaag aactgggcca aggctgcggc gttcgtgact    300
tcccctcccc tgagcccgga ccctaccacg cccgactact tgacctccct actggcctgt    360
ggggacttgc aggtcacagg cagcggccac tgtccctaca gcactgccca aaggcggtg    420 ggcaaggaca actttaccct gatccccgag ggtgtcaacg gatagagga gcggatgacg    480 gtcgtctggg acaaggcggt ggctactggc aaaatggatg agaaccagtt tgtcgctgtc    540
accagcacca atgcagccaa gatctttaac ctgtacccaa ggaaagggcg gattgccgtg    600
ggctcggatg ccgacgtggt catctgggac cccgacaagt tgaagaccat aacagccaaa    660
agtcacaagt cggcggtgga gtacaacatc ttcgagggta tggagtgcca cggctccccca    720 ctagtggtca tcagccaggg caagatcgtc tttgaagacg gaaacatcaa cgtcaacaag    780
ggcatgggcc gcttcattcc gcggaaggcg ttcccggagc acctgtacca gtagtctaga    840
a                                                                   841
```

<210> SEQ ID NO 19
<211> LENGTH: 167
<212> TYPE: PRT
<213> ORGANISM: Homo sapiens

<400> SEQUENCE: 19

```
Met Asp Tyr Leu Thr Ser Leu Leu Ala Cys Gly Asp Leu Gln Val Thr
 1               5                  10                  15

Gly Ser Gly His Cys Pro Tyr Ser Thr Ala Gln Lys Ala Val Gly Lys
            20                  25                  30

Asp Asn Phe Thr Leu Ile Pro Glu Gly Val Asn Gly Ile Glu Glu Arg
        35                  40                  45

Met Thr Val Val Trp Asp Lys Ala Val Ala Thr Gly Lys Met Asp Glu
    50                  55                  60

Asn Gln Phe Val Ala Val Thr Ser Thr Asn Ala Ala Lys Ile Phe Asn
65                  70                  75                  80

Leu Tyr Pro Arg Lys Gly Arg Ile Ala Val Gly Ser Asp Ala Asp Val
                85                  90                  95

Val Ile Trp Asp Pro Asp Lys Leu Lys Thr Ile Thr Ala Lys Ser His
            100                 105                 110

Lys Ser Ala Val Glu Tyr Asn Ile Phe Glu Gly Met Glu Cys His Gly
        115                 120                 125

Ser Pro Leu Val Val Ile Ser Gln Gly Lys Ile Val Phe Glu Asp Gly
    130                 135                 140

Asn Ile Asn Val Asn Lys Gly Met Gly Arg Phe Ile Pro Arg Lys Ala
145                 150                 155                 160

Phe Pro Glu His Leu Tyr Gln
                165
```

<210> SEQ ID NO 20
<211> LENGTH: 520
<212> TYPE: DNA
<213> ORGANISM: Homo sapiens

<400> SEQUENCE: 20

```
ctcgagacca tggactactt gacctcccta ctggcctgtg ggacttgca ggtcacaggc     60 agcggccact gtccctacag cactgcccag aaggcggtgg gcaaggacaa ctttaccctg   120
atccccgagg gtgtcaacgg gatagaggag cggatgacgg tcgtctggga caaggcggtg   180
```

```
gctactggca aaatggatga gaaccagttt gtcgctgtca ccagcaccaa tgcagccaag    240
atctttaacc tgtacccaag gaaagggcgg attgccgtgg gctcggatgc cgacgtggtc    300
atctgggacc ccgacaagtt gaagaccata acagccaaaa gtcacaagtc ggcggtggag    360
tacaacatct tcgagggtat ggagtgccac ggctccccac tagtggtcat cagccagggc    420
aagatcgtct tgaagacgg aaacatcaac gtcaacaagg gcatgggccg cttcattccg    480
cggaaggcgt tcccggagca cctgtaccag tagtctagaa                          520
```

<210> SEQ ID NO 21
<211> LENGTH: 116
<212> TYPE: PRT
<213> ORGANISM: Homo sapiens

<400> SEQUENCE: 21

```
Met Val Leu Val Gln Asp Lys Gly Val Asn Ser Phe Gln Val Tyr Met
  1               5                  10                  15

Ala Tyr Lys Asp Val Tyr Gln Met Ser Asp Ser Gln Leu Tyr Glu Ala
                 20                  25                  30

Phe Thr Phe Leu Lys Gly Leu Gly Ala Val Ile Leu Val His Ala Glu
             35                  40                  45

Asn Gly Asp Leu Ile Ala Gln Glu Gln Lys Arg Ile Leu Glu Met Gly
         50                  55                  60

Ile Thr Gly Pro Glu Gly His Ala Leu Ser Arg Pro Glu Glu Leu Glu
 65                  70                  75                  80

Ala Glu Ala Val Phe Arg Ala Ile Thr Ile Ala Gly Arg Ile Asn Cys
                 85                  90                  95

Pro Val Tyr Ile Thr Lys Val Met Ser Lys Ser Ala Ala Asp His His
                100                 105                 110

His His His His
        115
```

<210> SEQ ID NO 22
<211> LENGTH: 397
<212> TYPE: DNA
<213> ORGANISM: Homo sapiens

<400> SEQUENCE: 22

```
gaatactcat actcttccgg atccgtcgac gccaccatgg tgctggtgca ggacaaaggc     60
gtcaattcct tccaagtcta catggcctat aaggatgtct accaaatgtc cgacagccag    120
ctctatgaag cctttacctt ccttaagggc ctgggagctg tgatcttggt ccatgcagaa    180
aatggagatt tgatagctca ggaacaaaag cggatcctgg agatgggcat cacgggtccc    240
gagggccatg ccctgagcag acctgaagag ctggaggccg aggcggtgtt ccgggccatc    300
accattgcgg gccggatcaa ctgccctgtg tacatcacca aggtcatgag caagagtgca    360
gccgaccacc accatcacca ccactgagcg gccgctg                             397
```

<210> SEQ ID NO 23
<211> LENGTH: 123
<212> TYPE: PRT
<213> ORGANISM: Homo sapiens

<400> SEQUENCE: 23

```
Met Ile Ala Gln Glu Gln Lys Arg Ile Leu Glu Met Gly Ile Thr Gly
  1               5                  10                  15

Pro Glu Gly His Ala Leu Ser Arg Pro Glu Glu Leu Glu Ala Glu Ala
```

```
                    20                  25                  30
Val Phe Arg Ala Ile Thr Ile Ala Gly Arg Ile Asn Cys Pro Val Tyr
            35                  40                  45
Ile Thr Lys Val Met Ser Lys Ser Ala Ala Asp Ile Ile Ala Leu Ala
        50                  55                  60
Arg Lys Lys Gly Pro Leu Val Phe Gly Glu Pro Ile Ala Ala Ser Leu
65                  70                  75                  80
Gly Thr Asp Gly Thr His Tyr Trp Ser Lys Asn Trp Ala Lys Ala Ala
                85                  90                  95
Ala Phe Val Thr Ser Pro Pro Leu Ser Pro Asp Pro Thr Thr Pro Asp
            100                 105                 110
Tyr Leu Thr Ser Leu His His His His His His
        115                 120
```

<210> SEQ ID NO 24
<211> LENGTH: 418
<212> TYPE: DNA
<213> ORGANISM: Homo sapiens

<400> SEQUENCE: 24

```
gaatactcat actcttccgg atccgtcgac gccaccatga tagctcagga acaaaagcgg      60
atcctggaga tgggcatcac gggtcccgag ggccatgccc tgagcagacc tgaagagctg     120
gaggccgagg cggtgttccg ggccatcacc attgcgggcc ggatcaactg ccctgtgtac     180
atcaccaagg tcatgagcaa gagtgcagcc gacatcatcg ctctggccag gaagaaaggg     240
cccctagttt ttggagagcc cattgccgcc agcctgggga ccgatggcac ccattactgg     300
agcaagaact gggccaaggc tgcggcgttc gtgacttccc ctcccctgag cccggaccct     360
accacgcccg actacttgac ctccctacat catcaccatc atcactgagc ggccgcta      418
```

<210> SEQ ID NO 25
<211> LENGTH: 122
<212> TYPE: PRT
<213> ORGANISM: Homo sapiens

<400> SEQUENCE: 25

```
Met Asn Ile Asn Val Asn Lys Gly Met Gly Arg Phe Ile Pro Arg Lys
1               5                   10                  15
Ala Phe Pro Glu His Leu Tyr Gln Arg Val Lys Ile Arg Asn Lys Val
            20                  25                  30
Phe Gly Leu Gln Gly Val Ser Arg Gly Met Tyr Asp Gly Pro Val Tyr
        35                  40                  45
Glu Val Pro Ala Thr Pro Lys Tyr Ala Thr Pro Ala Pro Ser Ala Lys
    50                  55                  60
Ser Ser Pro Ser Lys His Gln Pro Pro Ile Arg Asn Leu His Gln
65                  70                  75                  80
Ser Asn Phe Ser Leu Ser Gly Ala Gln Ile Asp Asp Asn Asn Pro Arg
                85                  90                  95
Arg Thr Gly His Arg Ile Val Ala Pro Pro Gly Gly Arg Ser Asn Ile
            100                 105                 110
Thr Ser Leu Gly His His His His His
        115                 120
```

<210> SEQ ID NO 26
<211> LENGTH: 415
<212> TYPE: DNA
<213> ORGANISM: Homo sapiens

<400> SEQUENCE: 26

```
gaatactcat actcttccgg atccgtcgac gccaccatga acatcaacgt caacaagggc      60
atgggccgct tcattccgcg gaaggcgttc ccggagcacc tgtaccagcg cgtcaaaatc     120
aggaataagg tttttggatt gcaaggggtt tccaggggca tgtatgacgg tcctgtgtac     180
gaggtaccag ctacacccaa atatgcaact cccgctcctt cagccaaatc ttcgccttct     240
aaacaccagc ccccacccat cagaaacctc caccagtcca acttcagctt atcaggtgcc     300
cagatagatg acaacaatcc caggcgcacc ggccaccgca tcgtggcgcc ccctggtggc     360
cgctccaaca tcaccagcct cggtcatcat caccatcatc actgagcggc cgcta          415
```

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27

```
attgaaagct tatgtcgtac cagggca                                          27
```

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28

```
atatcctcga gaccgaggct ggtgatg                                          27
```

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29

```
agcaagcttg aacaaaagcg gatcctg                                          27
```

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30

```
taactcgagc tggtacaggt gctcc                                            25
```

<210> SEQ ID NO 31
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
tatgtacggt cgtaaaaaac gtcgtcagcg tcgtcgg 37

<210> SEQ ID NO 32
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gatcccgacg acgctgacga cgttttttac gaccgtaca 39

<210> SEQ ID NO 33
<211> LENGTH: 1440
<212> TYPE: DNA
<213> ORGANISM: Homo sapiens

<400> SEQUENCE: 33
atgtcgtacc agggcaagaa gagcatcccg cacatcacga gtgaccgact cctcatcaaa    60
ggtggacgga tcatcaacga tgaccaatcc ctttatgctg acgtctacct ggaggatgga   120
cttatcaaac aaataggaga gaacttaatc gttcctggtg gagtgaagac cattgaagcc   180
aacgggcgga tggttattcc cggaggtatt gatgtcaaca cgtacctgca gaagccctcc   240
caggggatga ctgcggctga tgacttcttc aagggaccag ggcggcact ggtgggcggg   300
accacgatga tcattgacca tgttgttcct gaacctgggt ccagcctact gacctctttc   360
gagaagtggc acgaagcagc tgacaccaaa tcctgctgtg attactccct ccacgtggac   420
atcacaagct ggtacgatgg cgttcgggag gagctggagg tgctggtgca ggacaaaggc   480
gtcaattcct tccaagtcta catggcctat aaggatgtct accaaatgtc cgacagccag   540
ctctatgaag cctttacctt ccttaagggc ctgggagctg tgatcttggt ccatgcagaa   600
aatggagatt tgatagctca ggaacaaaag cggatcctgg agatgggcat cacgggtccc   660
gagggccatg ccctgagcag acctgaagag ctggaggccg aggcggtgtt ccggccatc   720
accattgcgg gccggatcaa ctgccctgtg tacatcacca aggtcatgag caagagtgca   780
gccgacatca tcgctctggc caggaagaaa gggccctag ttttggaga gcccattgcc   840
gccagcctgg ggaccgatgg cacccattac tggagcaaga actgggccaa ggctgcggcg   900
ttcgtgactt cccctcccct gagcccggac cctaccacgc ccgactactt gacctcccta   960
ctggcctgtg gggacttgca ggtcacaggc agcggccact gtcccctacag cactgcccag  1020
aaggcggtgg gcaaggacaa ctttacccctg atccccgagg gtgtcaacgg gatagaggag  1080
cggatgacgg tcgtctggga caaggcggtg gctactggca aaatggatga gaaccagttt  1140
gtcgctgtca ccagcaccaa tgcagccaag atctttaacc tgtacccaag gaaagggcgg  1200
attgccgtgg gctcggatgc cgacgtggtc atctgggacc ccgacaagtt gaagaccata  1260
acagccaaaa gtcacaagtc ggcggtggag tacaacatct tcgagggtat ggagtgccac  1320
ggctccccac tagtggtcat cagccagggc aagatcgtct ttgaagacgg aaacatcaac  1380
gtcaacaagg gcatgggccg cttcattccg cggaaggcgt tcccggagca cctgtaccag  1440

<210> SEQ ID NO 34
<211> LENGTH: 819
<212> TYPE: DNA
<213> ORGANISM: Homo sapiens

<400> SEQUENCE: 34

```
gaacaaaagc ggatcctgga gatgggcatc acgggtcccg agggccatgc cctgagcaga      60
cctgaagagc tggaggccga ggcggtgttc cgggccatca ccattgcggg ccggatcaac     120
tgccctgtgt acatcaccaa ggtcatgagc aagagtgcag ccgacatcat cgctctggcc     180
aggaagaaag ggcccctagt ttttggagag cccattgccg ccagcctggg gaccgatggc     240
acccattact ggagcaagaa ctgggccaag gctgcggcgt tcgtgacttc ccctcccctg     300
agcccggacc ctaccacgcc cgactacttg acctccctac tggcctgtgg ggacttgcag     360
gtcacaggca gcggccactg tccctacagc actgcccaga aggcggtggg caaggacaac     420
tttaccctga tccccgaggg tgtcaacggg atagaggagc ggatgacggt cgtctgggac     480
aaggcggtgg ctactggcaa aatggatgag aaccagtttg tcgctgtcac cagcaccaat     540
gcagccaaga tctttaacct gtacccaagg aaagggcgga ttgccgtggg ctcggatgcc     600
gacgtggtca tctgggaccc cgacaagttg aagaccataa cagccaaaag tcacaagtcg     660
gcggtggagt acaacatctt cgagggtatg gagtgccacg gctccccact agtggtcatc     720
agccagggca gatcgtcttt tgaagacgga aacatcaacg tcaacaaggg catgggccgc     780
ttcattccgc ggaaggcgtt cccggagcac ctgtaccag                            819

<210> SEQ ID NO 35
<211> LENGTH: 498
<212> TYPE: DNA
<213> ORGANISM: Homo sapiens

<400> SEQUENCE: 35
gactacttga cctccctact ggcctgtggg gacttgcagg tcacaggcag cggccactgt      60
ccctacagca ctgcccagaa ggcggtgggc aaggacaact ttaccctgat ccccgagggt     120
gtcaacggga tagaggagcg gatgacggtc gtctgggaca aggcggtggc tactggcaaa     180
atggatgaga accagtttgt cgctgtcacc agcaccaatg cagccaagat ctttaacctg     240
tacccaagga aagggcggat tgccgtgggc tcggatgccg acgtggtcat ctgggacccc     300
gacaagttga agaccataac agccaaaagt cacaagtcgg cggtggagta caacatcttc     360
gagggtatgg agtgccacgg ctccccacta gtggtcatca gccagggcag atcgtctttt     420
gaagacggaa acatcaacgt caacaagggc atgggccgct tcattccgcg gaaggcgttc     480
ccggagcacc tgtaccag                                                  498

<210> SEQ ID NO 36
<211> LENGTH: 327
<212> TYPE: DNA
<213> ORGANISM: Homo sapiens

<400> SEQUENCE: 36
gtgctggtgc aggacaaagg cgtcaattcc ttccaagtct acatggccta aaggatgtc       60 taccaaatgt ccgacagcca gctctatgaa gcctttacct tccttaaggg cctgggagct     120
gtgatcttgg tccatgcaga aaatggagat ttgatagctc aggaacaaaa gcggatcctg     180
gagatgggca tcacgggtcc cgagggccat gccctgagca gacctgaaga gctggaggcc     240
gaggcggtgt tccgggccat caccattgcg ggccggatca actgccctgt gtacatcacc     300
aaggtcatga gcaagagtgc agccgac                                         327

<210> SEQ ID NO 37
<211> LENGTH: 348
<212> TYPE: DNA
```

<210> SEQ ID NO 37
<211> LENGTH: 348
<212> TYPE: DNA
<213> ORGANISM: Homo sapiens

<400> SEQUENCE: 37

```
atagctcagg aacaaaagcg gatcctggag atgggcatca cgggtcccga gggccatgcc      60
ctgagcagac ctgaagagct ggaggccgag gcggtgttcc gggccatcac cattgcgggc     120
cggatcaact gccctgtgta catcaccaag gtcatgagca agagtgcagc cgacatcatc     180
gctctggcca ggaagaaagg gcccctagtt tttggagagc ccattgccgc cagcctgggg     240
accgatggca cccattactg gagcaagaac tgggccaagg ctgcggcgtt cgtgacttcc     300
cctcccctga gccggaccc taccacgccc gactacttga cctcccta                   348
```

<210> SEQ ID NO 38
<211> LENGTH: 345
<212> TYPE: DNA
<213> ORGANISM: Homo sapiens

<400> SEQUENCE: 38

```
aacatcaacg tcaacaaggg catgggccgc ttcattccgc ggaaggcgtt cccggagcac      60
ctgtaccagc gcgtcaaaat caggaataag gttttttggat tgcaagggggt ttccagggggc    120
atgtatgacg gtcctgtgta cgaggtacca gctacaccca aatatgcaac tcccgctcct     180
tcagccaaat cttcgccttc taaacaccag ccccccaccca tcagaaacct ccaccagtcc     240
aacttcagct tatcaggtgc ccagatagat gacaacaatc ccaggcgcac cggccaccgc     300
atcgtggcgc cccctggtgg ccgctccaac atcaccagcc tcggt                    345
```

<210> SEQ ID NO 39
<211> LENGTH: 273
<212> TYPE: PRT
<213> ORGANISM: Homo sapiens

<400> SEQUENCE: 39

```
Glu Gln Lys Arg Ile Leu Glu Met Gly Ile Thr Gly Pro Glu Gly His
  1               5                  10                  15

Ala Leu Ser Arg Pro Glu Glu Leu Glu Ala Glu Ala Val Phe Arg Ala
             20                  25                  30

Ile Thr Ile Ala Gly Arg Ile Asn Cys Pro Val Tyr Ile Thr Lys Val
         35                  40                  45

Met Ser Lys Ser Ala Ala Asp Ile Ile Ala Leu Ala Arg Lys Lys Gly
     50                  55                  60

Pro Leu Val Phe Gly Glu Pro Ile Ala Ala Ser Leu Gly Thr Asp Gly
 65                  70                  75                  80

Thr His Tyr Trp Ser Lys Asn Trp Ala Lys Ala Ala Ala Phe Val Thr
                 85                  90                  95

Ser Pro Pro Leu Ser Pro Asp Pro Thr Thr Pro Asp Tyr Leu Thr Ser
            100                 105                 110

Leu Leu Ala Cys Gly Asp Leu Gln Val Thr Gly Ser Gly His Cys Pro
        115                 120                 125

Tyr Ser Thr Ala Gln Lys Ala Val Gly Lys Asp Asn Phe Thr Leu Ile
    130                 135                 140

Pro Glu Gly Val Asn Gly Ile Glu Glu Arg Met Thr Val Val Trp Asp
145                 150                 155                 160

Lys Ala Val Ala Thr Gly Lys Met Asp Glu Asn Gln Phe Val Ala Val
                165                 170                 175

Thr Ser Thr Asn Ala Ala Lys Ile Phe Asn Leu Tyr Pro Arg Lys Gly
            180                 185                 190
```

```
Arg Ile Ala Val Gly Ser Asp Ala Asp Val Val Ile Trp Asp Pro Asp
            195                 200                 205

Lys Leu Lys Thr Ile Thr Ala Lys Ser His Lys Ser Ala Val Glu Tyr
210                 215                 220

Asn Ile Phe Glu Gly Met Glu Cys His Gly Ser Pro Leu Val Val Ile
225                 230                 235                 240

Ser Gln Gly Lys Ile Val Phe Glu Asp Gly Asn Ile Asn Val Asn Lys
                245                 250                 255

Gly Met Gly Arg Phe Ile Pro Arg Lys Ala Phe Pro Glu His Leu Tyr
            260                 265                 270

Gln

<210> SEQ ID NO 40
<211> LENGTH: 166
<212> TYPE: PRT
<213> ORGANISM: Homo sapiens

<400> SEQUENCE: 40

Asp Tyr Leu Thr Ser Leu Leu Ala Cys Gly Asp Leu Gln Val Thr Gly
1               5                   10                  15

Ser Gly His Cys Pro Tyr Ser Thr Ala Gln Lys Ala Val Gly Lys Asp
                20                  25                  30

Asn Phe Thr Leu Ile Pro Glu Gly Val Asn Gly Ile Glu Glu Arg Met
            35                  40                  45

Thr Val Val Trp Asp Lys Ala Val Ala Thr Gly Lys Met Asp Glu Asn
        50                  55                  60

Gln Phe Val Ala Val Thr Ser Thr Asn Ala Ala Lys Ile Phe Asn Leu
65                  70                  75                  80

Tyr Pro Arg Lys Gly Arg Ile Ala Val Gly Ser Asp Ala Asp Val Val
                85                  90                  95

Ile Trp Asp Pro Asp Lys Leu Lys Thr Ile Thr Ala Lys Ser His Lys
            100                 105                 110

Ser Ala Val Glu Tyr Asn Ile Phe Glu Gly Met Glu Cys His Gly Ser
        115                 120                 125

Pro Leu Val Val Ile Ser Gln Gly Lys Ile Val Phe Glu Asp Gly Asn
    130                 135                 140

Ile Asn Val Asn Lys Gly Met Gly Arg Phe Ile Pro Arg Lys Ala Phe
145                 150                 155                 160

Pro Glu His Leu Tyr Gln
                165

<210> SEQ ID NO 41
<211> LENGTH: 109
<212> TYPE: PRT
<213> ORGANISM: Homo sapiens

<400> SEQUENCE: 41

Val Leu Val Gln Asp Lys Gly Val Asn Ser Phe Gln Val Tyr Met Ala
1               5                   10                  15

Tyr Lys Asp Val Tyr Gln Met Ser Asp Ser Gln Leu Tyr Glu Ala Phe
                20                  25                  30

Thr Phe Leu Lys Gly Leu Gly Ala Val Ile Leu Val His Ala Glu Asn
            35                  40                  45

Gly Asp Leu Ile Ala Gln Glu Gln Lys Arg Ile Leu Glu Met Gly Ile
        50                  55                  60
```

```
Thr Gly Pro Glu Gly His Ala Leu Ser Arg Pro Glu Glu Leu Glu Ala
 65                  70                  75                  80

Glu Ala Val Phe Arg Ala Ile Thr Ile Ala Gly Arg Ile Asn Cys Pro
             85                  90                  95

Val Tyr Ile Thr Lys Val Met Ser Lys Ser Ala Ala Asp
        100                 105
```

<210> SEQ ID NO 42
<211> LENGTH: 116
<212> TYPE: PRT
<213> ORGANISM: Homo sapiens

<400> SEQUENCE: 42

```
Ile Ala Gln Glu Gln Lys Arg Ile Leu Glu Met Gly Ile Thr Gly Pro
 1               5                  10                  15

Glu Gly His Ala Leu Ser Arg Pro Glu Glu Leu Glu Ala Glu Ala Val
             20                  25                  30

Phe Arg Ala Ile Thr Ile Ala Gly Arg Ile Asn Cys Pro Val Tyr Ile
         35                  40                  45

Thr Lys Val Met Ser Lys Ser Ala Ala Asp Ile Ile Ala Leu Ala Arg
     50                  55                  60

Lys Lys Gly Pro Leu Val Phe Gly Glu Pro Ile Ala Ala Ser Leu Gly
 65                  70                  75                  80

Thr Asp Gly Thr His Tyr Trp Ser Lys Asn Trp Ala Lys Ala Ala Ala
             85                  90                  95

Phe Val Thr Ser Pro Pro Leu Ser Pro Asp Pro Thr Thr Pro Asp Tyr
        100                 105                 110

Leu Thr Ser Leu
        115
```

<210> SEQ ID NO 43
<211> LENGTH: 115
<212> TYPE: PRT
<213> ORGANISM: Homo sapiens

<400> SEQUENCE: 43

```
Asn Ile Asn Val Asn Lys Gly Met Gly Arg Phe Ile Pro Arg Lys Ala
 1               5                  10                  15

Phe Pro Glu His Leu Tyr Gln Arg Val Lys Ile Arg Asn Lys Val Phe
             20                  25                  30

Gly Leu Gln Gly Val Ser Arg Gly Met Tyr Asp Gly Pro Val Tyr Glu
         35                  40                  45

Val Pro Ala Thr Pro Lys Tyr Ala Thr Pro Ala Pro Ser Ala Lys Ser
     50                  55                  60

Ser Pro Ser Lys His Gln Pro Pro Ile Arg Asn Leu His Gln Ser
 65                  70                  75                  80

Asn Phe Ser Leu Ser Gly Ala Gln Ile Asp Asp Asn Asn Pro Arg Arg
             85                  90                  95

Thr Gly His Arg Ile Val Ala Pro Pro Gly Gly Arg Ser Asn Ile Thr
        100                 105                 110

Ser Leu Gly
       115
```

<210> SEQ ID NO 44
<211> LENGTH: 6
<212> TYPE: PRT
<213> ORGANISM: Artificial Sequence
<220> FEATURE:

```
-continued

<223> OTHER INFORMATION: Description of Artificial Sequence: Synthetic
      6xHis tag

<400> SEQUENCE: 44

His His His His His His
  1               5

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Tyr Gly Arg Lys Lys Arg Arg Gln Arg Arg Arg
  1               5                  10
```

COMPOSITIONS AND METHODS OF USING CRMP-1 AND ITS FRAGMENTS FOR TREATING CANCER

PRIORITY CLAIM

This application claims the priority of U.S. Provisional Application Ser. No. 60/907,189, filed on Mar. 23, 2007, which is herein incorporated by reference.

BACKGROUND OF THE INVENTION

The present invention relates to active fragments of collapsin response mediator protein-1 (CRMP-1), methods for treating cancer with active fragments of hCRMP-1, and methods for inhibiting the proliferation of cancer using CRMP-1 and active fragments of CRMP-1.

Collapsin response mediator protein-1 (CRMP-1), also named as dihydropyrimidinase related protein-1 (DRP-1), is a 62 kDa phosphoprotein. CRMP-1 was originally discovered in the brain tissue and thought to be a brain specific protein involved in the collapsin-induced growth cone collapse during neural development. Torres et al., *DNA Res.*, 5(6): 393-395 (1998).

Collapsin response mediator proteins (CRMPs) belong to a family of phosphoproteins, which mediate semaphorin/collapsin-induced growth cone collapse and are believed to be involved in both axonal guidance and neuronal differentiation. CRMPs are expressed mainly in the nervous system, especially during embryogenesis. Immunocytochemical studies have shown that CRMPs are distributed in the lamellipodia and filopodia of the growth cone, the shaft of axons, and the neuronal cell body. Their expression and phosphorylation are spatially and temporally regulated during development although their molecular mechanisms of action are yet to be clearly.

The members of CRMPs bear the sequence homology to UNC-33, a nematode protein, whose absence produces aberrant elongation of axons and uncoordinated movement in the worm *Caenorhabditis elegans*. Li et al., *Genetics*, 132(3): 675-689 (1992). CRMP family members have a 50%-70% amino acid sequence homology. Five members of the CRMP gene family (crmp-1, crmp-2, crmp-3, crmp-4, and crmp-5), encoding closely related 60-66 kDa proteins, have been independently cloned by various laboratories. Each CRMP is believed to have a unique function. The members of the CRMP family have been referred to as CRMP (collapsin response mediator protein), TOAD-64 (turned on after division of a 64 kD protein), Ulip (UNC-33 like phosphoprotein), DRP (dihydropyrimidinase related protein) and TUC (TOAD/Ulip/CRMP). Nonetheless, the most frequently used name in medical literature is CRMP.

Transcription of the ORMP gene is differentially regulated. Inaaaki et al., *Histochem. Cell Biol.*, 113: 37-41 (2000); Matsuo et al., *J. Biol. Chem.*, 275(22): 16560-16568 (2000); Quach et al., *Gene*, 242(1-2): 175-182 (2000). Mouse CRMP-1, CRMP-4 and CRMP-5 are mainly expressed in the fetal brain and not in the brain of the adult mice. On the other hand, CRMP-2 and CRMP-3 are expressed in the brain of both the fetal and the adult mice. However, in the adult mice, CRMP-3 is localized in the cerebellum. In PC-12 cells, after induction of neuronal differentiation by nerve growth factor (NGF), CRMP-4 was strongly up-regulated, whereas CRMP-1 and CRMP-2 only increased slightly and CRMP-3 was down-regulated. Byk et al., *Eur. J. Biochem.* 254:14-24(1998). At this time, only the promoter of human CRMP-4 has been isolated and analyzed. Matsuo et al., *J. Biol. Chem.*, 275(22): 16560-16568 (2000). No studies of the regulatory elements of other members of the CRMP family have been conducted.

Recent works reported that the level of expression of the gene encoding human CRMP-1 (hereinafter "hCRMP-1 gene") inversely affects cancer invasion and metastasis, (i.e., the higher the level of expression, the lower the incidence of cancer invasion and metastasis) and thus characterized the human CRMP-1 gene as an invasion-suppression gene. The following studies found that low-expression patients of hCRMP-1 had more advanced diseases and lymph node metastases, while high-expression patients of hCRMP-1 had a significantly longer disease-free and overall survival period. Shih et al., *J. Natl. Cancer Inst.*, 93(18): 1392-1400 (2001); Chu et al., *Am. J. Respir. Cell Mol. Biol.*, 17: 353-360 (1997); and Shih et al., *Clinical & Exper. Metastasis*, 20: 69-76 (2003).

However, the reports cited above only examined the biological activities of full-length hCRMP-1 protein; the effect of fragments of hCRMP-1 was unknown and the active portions of the full-length protein had not been identified. Further, the prior art only reported the effect of CRMP-1 on metastasis and invasion; any effect on cell proliferation had not been identified.

In accordance with the present invention, certain active fragments have now been discovered and are advantageous in that they can be produced much more easily than the full-length CRMP-1 and in larger quantities, yet still retain all or most of the original biological activities against tumor cells. This would make commercial production more economically and technically feasible.

In addition, it is surprising that certain active fragments achieve better and broader antiproliferative effect on cancer cells than the full-length CRMP-1. For example, CN3, as discussed herein, shows certain improved results over full-length hCRMP-1. Other fragments also exhibit better selectivity in antiproliferative effect on cancer cells than the full-length CRMP-1. For example, the CN5 and CN7 fragments showed good selectivity in inhibiting growth of lung cancer cells while not affecting the growth of normal cells. Such selectivity was not observed when using the full-length CRMP-1. In addition, where the full-length CRMP-1 protein showed suppression of growth of normal cells, certain fragments such as CN5 showed no such side effect, further illustrating that these fragments have advantages over the prior art. There has thus been a long-felt and unfulfilled need in the art to identify active fragments of CRMP-1 so as to allow the large-scale production of protein fragments having the same or better activity as the full-length protein.

Additionally, there has been a need to identify additional agents that act on cell proliferation. As discussed above, it was previously believed that full-length CRMP-1 did not inhibit cell proliferation based on studies in lung cancer cells; however, it has now been determined that full-length CRMP-1 inhibits proliferation in prostate cancer, colon cancer, and breast cancer. It has also been determined that, despite prior studies, full-length CRMP-1 inhibits lung cancer cells to a lesser extent. For example, using poorly differenciated human lung adenocarcinoma cells established from a patient, Shih et al. observed no antiproliferative activity of full-length CRMP-1, see *J. Natl. Cancer Inst.*, 93(18): 1392-1400 (2001). In contrast, our experiments showed full-length CRMP-1 has antiproliferative activity towards the human lung large-cell carcinoma cells H460.

SUMMARY OF INVENTION

An aspect of the invention includes an active fragment of CRMP-1 comprising an amino acid sequence chosen from SEQ ID NO: 15, 17, 19, 21, 23, 25, and 39-43, wherein the fragment inhibits the proliferation, metastasis, and/or invasion of cancer and further wherein the active fragment is from 109 to 500 amino acids in length. In certain embodiments, the active fragment comprises SEQ ID NO: 17. In additional embodiments, the fragment is a fusion protein further comprising a TAT sequence.

In yet other embodiments, the active fragment comprises an amino acid sequence chosen from sequences at least 95% identical to SEQ ID NO: 15, 17, 19, 21, 23, 25, and 39-43 wherein the active fragment inhibits the proliferation, metastasis, and/or invasion of cancer and further wherein the active fragment is from 109 to 500 amino acids in length.

Another embodiment of the invention further includes a nucleic acid sequence encoding an active fragment of CRMP-1 comprising a sequence chosen from SEQ ID NO: 16, 18, 20, 22, 24, 26, 33, 34, 35, 36, 37, and 38, wherein the active fragment inhibits the proliferation, metastasis, and/or invasion of cancer and further wherein the nucleic acid sequence is from 327 to 1500 nucleic acids in length. In certain embodiments, the nucleic acid sequence comprises SEQ ID NO: 18. In other embodiments, the nucleic acid sequence encodes a fusion protein of the active fragment of CRMP-1 and a TAT sequence.

In other embodiments, the invention includes a nucleic acid sequence encoding an active fragment of CRMP-1 comprising a nucleic acid sequence chosen from sequences at least 95% identical to SEQ ID NO: 16, 18, 20, 22, 24, 26, 33, 34, 35, 36, 37, and 38, wherein the active fragment inhibits the proliferation, metastasis, and/or invasion of cancer and further wherein the nucleic acid sequence is from 327 to 1440 nucleic acids in length.

One embodiment of the invention further comprises a method for treating cancer comprising administering the active fragment of CRMP-1 of claim 1 to a patient in need thereof and allowing the active fragment of CRMP-1 to inhibit the proliferation, metastasis, and/or invasion of the cancer cells.

In yet another embodiment, the active fragment of CRMP-1 is administered substantially concurrently with a chemotherapeutic agent and wherein the active fragment of CRMP-1 further enhances the effectiveness of the chemotherapeutic agent, such as, but not limited to, paclitaxel.

In a further embodiment, the invention includes a method of inhibiting the proliferation of cancer comprising administering CRMP-1 to a patient in need thereof and allowing the CRMP-1 to inhibit proliferation of the cancer cell.

Additionally, one embodiment of the invention includes a vector for expression of an active fragment of CRMP-1 comprising:
  (a) at least one regulatory element and
  (b) an encoding portion consisting essentially of a nucleic acid sequence encoding an active fragment of CRMP-1 comprising a sequence chosen from SEQ ID NO: 16, 18, 20, 22, 24, 26, 33, 34, 35, 36, 37, and 38, wherein the active fragment inhibits the proliferation, metastasis, and/or invasion of cancer and further wherein the encoding portion of the vector is from 327 to 1440 nucleic acids in length. Variants of the active fragments of CRMP-1 may also be utilized in the vector.

In certain embodiments the vector is a viral vector, and in other embodiments it is chosen from an astrovirus, coronavirus, orthomyxovirus, papovavirus, paramyxovirus, parvovirus, picornavirus, poxvirus, or togavirus viral vector. In other embodiments, at least one regulatory element is a tissue-specific regulatory element.

DESCRIPTION OF THE FIGURES

FIG. 1 shows the amino acid sequence of human CRMP-1 (SEQ ID NO: 1).

FIG. 2 shows the nucleic acid sequence of the gene encoding human CRMP-1 (SEQ ID NO: 2, GenBank Accession No. D78012, NCBI). This sequence is a cDNA sequence.

FIG. 3 shows the nucleic acid sequence (SEQ ID NO: 3) of a forward primer used in PCR to amplify hCRMP-1.

FIG. 4 shows the nucleic acid sequence (SEQ ID NO: 4) of a reverse primer used in PCR to amplify hCRMP-1.

FIG. 5 shows the nucleic acid sequence (SEQ ID NO: 5) of a primer used for construction of the CN1 DNA fragment of hCRMP-1.

FIG. 6 shows the nucleic acid sequence (SEQ ID NO: 6) of a primer used for construction of the CN3 DNA fragment of hCRMP-1.

FIG. 7 shows the nucleic acid sequence (SEQ ID NO: 7) of a primer used for construction of the CN4 DNA fragment corresponding to CN4 domain of hCRMP-1.

FIG. 8 shows the nucleic acid sequence (SEQ ID NO: 8) of a reverse primer used for construction of the CN1, CN3, and CN4 DNA fragments of hCRMP-1.

FIG. 9 shows the nucleic acid sequence (SEQ ID NO: 9) of a forward primer used for construction of the CN5 DNA fragment of hCRMP-1.

FIG. 10 shows the nucleic acid sequence (SEQ ID NO: 10) of a forward primer used for construction of the CN6 DNA fragment of hCRMP-1.

FIG. 11 shows the nucleic acid sequence (SEQ ID NO: 11) of a forward primer used for construction of the CN7 DNA fragment of hCRMP-1.

FIG. 12 shows the nucleic acid sequence (SEQ ID NO: 12) of a reverse primer used for construction of the CN5 DNA fragment of hCRMP-1.

FIG. 13 shows the nucleic acid sequence (SEQ ID NO: 13) of a reverse primer used for construction of the CN6 DNA fragment of hCRMP-1.

FIG. 14 shows the nucleic acid sequence (SEQ ID NO: 14) of a reverse primer used for construction of the CN7 DNA fragment of hCRMP-1.

FIG. 15 shows the amino acid sequence (SEQ ID NO: 15) of the CN1 domain of hCRMP-1.

FIG. 16 shows the nucleic acid sequence (SEQ ID NO: 16) used to construct the CN1 domain of hCRMP-1.

FIGS. 17A-B shows the amino acid sequence (SEQ ID NO: 17 and 39) of the CN3 domain of hCRMP-1, with and without a N-terminal methionine, respectively.

FIG. 18 shows the nucleic acid sequence (SEQ ID NO: 18) used to construct the CN3 domain of hCRMP-1.

FIGS. 19A-B shows the amino acid sequence (SEQ ID NO: 19 and 40) of the CN4 domain of hCRMP-1, with and without a N-terminal methionine, respectively.

FIG. 20 shows the nucleic acid sequence (SEQ ID NO: 20) used to construct the CN4 domain of hCRMP-1.

FIGS. 21A-B shows the amino acid sequence (SEQ ID NO: 21 and 41) of the CN5 domain of hCRMP-1, with and without both a N-terminal methionine and a C-terminal His tag, respectively.

FIG. 22 shows the nucleic acid sequence (SEQ ID NO: 22) used to construct the CN5 domain of hCRMP-1.

FIGS. 23A-B shows the amino acid sequence (SEQ ID NO: 23 and 42) of the CN6 domain of hCRMP-1, with and without both a N-terminal methionine and a C-terminal His tag, respectively.

FIG. 24 shows the nucleic acid sequence (SEQ ID NO: 24) used to construct the CN6 domain of hCRMP-1.

FIGS. 25A-B shows the amino acid sequence (SEQ ID NO: 25 and 43) of the CN7 domain of hCRMP-1, with and without both a N-terminal methionine and a C-terminal His tag, respectively.

FIG. 26 shows the nucleic acid sequence (SEQ ID NO: 26) used to construct the CN7 domain of hCRMP-1.

FIG. 27 shows the nucleic acid sequence (SEQ ID NO: 27) of a forward primer for heterologous expression of hCRMP-1 in *E. coli*.

FIG. 28 shows the nucleic acid sequence (SEQ ID NO: 28) of a reverse primer for heterologous expression of hCRMP-1 in *E. coli*.

FIG. 29 shows the nucleic acid sequence (SEQ ID NO: 29) of a forward primer for heterologous expression of the CN3 domain of hCRMP-1 in *E. coli*.

FIG. 30 shows the nucleic acid sequence (SEQ ID NO: 30) of a reverse primer for heterologous expression of the CN3 domain of hCRMP-1 in *E. coli*.

FIG. 31 shows the nucleic acid sequence (SEQ ID NO: 31) of a nucleotide fragment used for construction of expression plasmid pETAT.

FIG. 32 shows the nucleic acid sequence (SEQ ID NO: 32) of a nucleotide fragment used for construction of expression plasmid pETAT.

FIG. 33 shows the nucleic acid sequence (SEQ ID NO: 33) encoding the CN1 domain of hCRMP-1.

FIG. 34 shows the nucleic acid sequence (SEQ ID NO: 34) encoding the CN3 domain of hCRMP-1.

FIG. 35 shows the nucleic acid sequence (SEQ ID NO: 35) encoding the CN4 domain of hCRMP-1.

FIG. 36 shows the nucleic acid sequence (SEQ ID NO: 36) encoding the CN5 domain of hCRMP-1.

FIG. 37 shows the nucleic acid sequence (SEQ ID NO: 37) encoding the CN6 domain of hCRMP-1.

FIG. 38 shows the nucleic acid sequence (SEQ ID NO: 38) encoding the CN7 domain of hCRMP-1.

DETAILED DESCRIPTION OF THE INVENTION

I. Active Fragments of CRMP-1

One aspect of the present invention includes active fragments of CRMP-1 with no more than 500 amino acids, which have retained and in some instances even exceeded the activity of the full-length CRMP-1 protein. These fragments have been named CN1, CN3, CN4, CN5, CN6, and CN7. The active fragments of the invention inhibit proliferation, metastasis, and invasion of cancer. While not limited to activity in the certain cell types, the following activities have been shown.

TABLE 1

REPRESENTATIVE ACTIVE FRAGMENTS

| Fragment Name | Figures | SEQ ID NOS. | Relationship to full-length hCRMP-1* | Activity/ Tissue Type Demonstrated |
|---|---|---|---|---|
| CN1 | FIG. 15 | SEQ ID NO: 15 | 1-480 of SEQ ID NO: 1 | some inhibition to lung cancer cells |
| CN3 | FIG. 17A-B | SEQ ID NOS: 17 and 39 | 208-480 of SEQ ID NO: 1 | colon cancer cell CC-M1 and DLD-1; lung cancer cell H520; prostate cancer cells PC-3 and DU145; breast cancer cell MCF-7 |
| CN4 | FIG. 19A-B | SEQ ID NOS: 19 and 40 | 315-480 of SEQ ID NO: 1 | some inhibition to lung cancer cells |
| CN5 | FIG. 21A-B | SEQ ID NOS: 21 and 41 | 154-262 of SEQ ID NO: 1 | lung cancer cell H520, with no observed side effect to normal cell; colon cancer cells CC-M1 and DLD-1 ; breast cancer cell MCF-7 |
| CN6 | FIG. 23A-B | SEQ ID NOS: 23 and 42 | 205-320 of SEQ ID NO: 1 | prostate cancer cell DU145; breast cancer cell MCF-7; colon cancer cell CC-M1 and some inhibition to colon cancer cell DLD-1 |
| CN7 | FIG. 25A-B | SEQ ID NOS: 25 and 43 | 458-572 of SEQ ID NO: 1 | lung cancer cell H520, with no side effect to normal cells; breast cancer cell MCF-7; prostate cancer cell DU145; colon cancer cell DLD-1 |

*Certain figures and sequences contain an N-terminal methionine, or both an N-terminal methionine and a C-terminal His tag, that are not present in the native sequence and reference positions exclude these additional elements.

Active fragments of the invention also include sequences with addition, deletion, or substitution mutations when compared to the sequence identified in the table above. Such active fragments may be at least 80%, 90%, 91%, 92%, 93%, 94%, 95%, 96%, 97%, 98%, or 99% identical to the sequences specifically identified in this application (as shown in FIGS. 15, 17, 19, 21, 23, and 25).

Variants of active fragments also include conservative substitutions, which are substitutions of amino acids of the same category, such as substitutions of amino acids with non-charged side-chains (such as asparagine, glutamine, serine, threonine and tyrosine), of amino acids with basic side-chains (such as lysine, arginine and histidine), of amino acids with acid side-chains (such as aspartic acid and glutamic acid), and of amino acids with apolar side-chains (such as glycine, alanine, valine, leucine, isoleucine, proline, phenylalanine, methionine, tryptophan and cysteine). Additionally, variants include substitution of natural amino acids with unnatural amino acids or pseudo amino acids, in positions such that these modifications do not significantly impair the biological activity of the active fragments.

In certain embodiments the active fragments are 480, 273, 166, 116, 115, 109 amino acids or shorter. In other embodiments, the active fragments are from 100 to 500, 125 to 475, 150 to 450, 175 to 425, 200 to 400, 225 to 375, 250 to 350, 260 to 340, or 275 to 325 amino acids long. In yet other embodiments the fragments are 500, 475, 450, 425, 375, 350, 325, 300, 275, 250, 225, 200, 175, 150, or 125 amino acids or shorter.

Such variants may be prepared recombinantly or may be derived from CRMP-1 variants from other species. Thus, the CRMP-1 of the invention may be of human origin, or from non-human primates, rat, or mice species.

Some CRMP-1 fragments contain one additional methionine (represented as symbol "M" in amino acid sequence listings) in the expression construct in order to build an "open reading frame" and can be expressed as protein in mammalian cells or in prokaryote cell (e.g. $E.$ $coli$). In some embodiments of the invention, methionine residues may be added to the beginning of each fragment; in other embodiments, they may be removed. It is specifically envisioned as an embodiment of the invention that each sequence described or shown herein with a methionine residue may be constructed without one; likewise each sequence shown without this element may be constructed with it.

In other embodiments, fusion proteins can be prepared to increase the effectiveness or stability of the active fragments of the invention. For example, the active fragments of the invention can be fused to a transcriptional activator of transcription (TAT) sequence. TAT is an 86-amino acid protein involved in the replication of human immunodeficiency virus type-1 (HIV-1). Studies have shown that the TAT protein has a unique potential to enter cells in culture when added exogenously, see Harada et al., $Breast$ $Cancer$, Vol. 13(1): 16-26 (2006). The TAT peptide has been used extensively for directing the intracellular delivery of macromolecules for treatment. A variety of TAT-fusion proteins have been described which link the TAT coding sequence to the protein coding sequence of interest, see, Albarran et al., $Protein$ $Engineering,$ $Design$ $&$ $Selection$, Vol. 18(3): 147-152 (2005). Conjugation of the active fragments, such as CN3, to the TAT sequence may improve translocation of the fragments into the cancer cells and, hence, increase the efficacy of the active fragments. It is specifically envisioned as an embodiment of the invention that each sequence described or shown herein with a TAT-fusion may be constructed without this element; likewise each sequence shown without a TAT-fusion may be constructed with it.

In another embodiment, a His tag may be affixed to the fragment using recombinant technologies to aid in protein purification. In one embodiment, the His tag may have 4, 5, 6, 7, 8, 9, or 10 His residues. It is specifically envisioned as an embodiment of the invention that each sequence described or shown herein with a His tag may be constructed without one; likewise each sequence shown without this element may be constructed with it.

II. Nucleic Acid Sequences Encoding the Active Fragments of CRMP-1

The invention also includes isolated nucleic acids encoding the hCRMP-1 active fragments of CRMP-1 (i.e., CN1, CN3, CN4, CN5, CN6, and CN7); such nucleic acids have no more than 1500 bases. Representative sequences encoding these fragments are identified in the following table. As is common in the art, the nucleic acids were amplified using PCR primers, therefore, in certain embodiments additional non-coding primer sequences are included in the invention on the 3' and/or 5' end, as shown in the table as well. In other embodiments, the nucleic acids exactly encode the fragments without any N-terminal methionine or C-terminal His tag. Additionally, owing to the degeneracy of the genetic code, additional sequences are contemplated that encode the same amino acid sequences. As discussed above, regarding the amino acid sequences, it is specifically envisioned as an embodiment of the invention that each sequence described or shown herein encoding a methionine, TAT fusion, and/or His tag may be constructed without one; likewise each sequence shown without these elements may be constructed with them.

TABLE 2

NUCLEIC ACIDS ENCODING ACTIVE FRAGMENTS

| Fragment | Containing Additional Non-Coding Primer Sequences on 3' and/or 5' End* | | Exactly Encoding Fragment Without Non-Coding Primer, Added N-terminal Methionine** or C-terminal His Tag | |
|---|---|---|---|---|
| Name | Figure | SEQ ID NO | Figure | SEQ ID NO |
| CN1 | FIG. 16 | SEQ ID NO: 16 | FIG. 33 | SEQ ID NO: 33 |
| CN3 | FIG. 18 | SEQ ID NO: 18 | FIG. 34 | SEQ ID NO: 34 |
| CN4 | FIG. 20 | SEQ ID NO: 20 | FIG. 35 | SEQ ID NO: 35 |
| CN5 | FIG. 22 | SEQ ID NO: 22 | FIG. 36 | SEQ ID NO: 36 |
| CN6 | FIG. 24 | SEQ ID NO: 24 | FIG. 37 | SEQ ID NO: 37 |
| CN7 | FIG. 26 | SEQ ID NO: 26 | FIG. 38 | SEQ ID NO: 38 |

*Certain of these sequences also contain an additional ATG encoding for methionine that is not present in the corresponding portion of the CRMP-1 full-length sequence, or an additional methionine encoding ATG and a His tag encoding portion.
**For FIG. 33 and SEQ ID NO: 33 an ATG encoding methionine is included because the N-terminus of CN1 corresponds to the N-terminus of the CRMP-1 full-length protein.

The various nucleotide or peptide sequences of the invention may be of artificial or non-artificial origin. They may be DNA or RNA sequences, obtained by screening sequence banks by means of probes developed on the basis of the original sequences. Banks of this type may be prepared by conventional techniques of molecular biology known to a person skilled in the art.

The nucleotide sequences according to the invention may also be prepared by chemical synthesis or alternatively by mixed methods, including the chemical or enzymatic modification of sequences obtained by screening bands. These nucleotide sequences permit the production of nucleotide probes that are capable of hybridizing strongly and specifically with a sequence of nucleic acids, of a genomic DNA or a messenger RNA encoding a peptide according to the invention, or an active fragment thereof.

Nucleic acids encoding the active fragments of the invention also include sequences with addition, deletion, or substitution mutations when compared to the sequences identified in the table above, such nucleic acid sequences may be sequences at least 80%, 90%, 91%, 92%, 93%, 94%, 95%, 96%, 97%, 98%, or 99% identical to the sequences identified in this application (as shown in FIGS. 16, 18, 20, 22, 24, and 26).

Such variants may be prepared recombinantly or may be derived from CRMP-1 variants from other species. Thus, the CRMP-1 of the invention may be of human origin, or from non-human primates, rat, or mice species.

Additionally, sequences hybridizing with sequences shown in FIGS. 16, 18, 20, 22, 24, and 26, or their complementary sequences under stringent conditions are included in this invention. Stringent conditions include, for example, 0.5 M $NaHPO_4$, 7% sodium dodecyl sulfate (SDS), 1 mM EDTA at 65° C., and washing in 0.2×SSC/0.1% SDS at 42° C. (see Ausubel, et al (eds), 1989, Current Protocols in Molecular Biology, Vol. 1, Green Publishing Associates, Inc., and John Wiley & Sons, Inc., New York, at p. 2.10.3). Alternatively, stringent conditions may, for example, include 0.5 M $NaHPO_4$, 7% SDS, 1 mM EDTA at 65° C., and washing in 0.1×SSC/0.1% SDS at 68° C. (see Ausubel, et al (eds), 1989, Current Protocols in Molecular Biology, Vol. 1, Green Publishing Associates, Inc., and John Wiley & Sons, Inc., New York, at p. 2.10.3). Hybridization conditions may be modified in accordance with known methods depending on the sequence of interest (see Tijssen, 1993, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, N.Y.). Generally, stringent conditions are selected to be about 5° C. lower than the thermal melting point for the specific sequence at a defined ionic strength and pH. Stringent hybridization may, for example, be in 5×SSC and 50% formamide at 42° C. and washing in a wash buffer consisting of 0.1×SSC at 65° C. Washes for stringent hybridization may for example be of at least 15 minutes, 30 minutes, 45 minutes, 60 minutes, 75 minutes, 90 minutes, 105 minutes or 120 minutes.

In certain embodiments, the active fragments are 1440, 819, 498, 348, 345, 327 nucleic acids or shorter. In other embodiments, the active fragments are from 300 to 1500, 375 to 1425, 450 to 1350, 525 to 1275, 600 to 1200, 675 to 1125, 750 to 1050, 780 to 1020, 825 to 975, 300 to 900, 325 to 500, 375 to 525, or 300 to 400 nucleic acids long. In yet other embodiments the fragments are 1500, 1425, 1350, 1275, 1125, 1050, 755, 900, 825, 750, 675, 600, 525, 450, or 375 nucleic acids or shorter.

III. Methods of Using the Active Fragments of CRMP-1

A. Method of Treatment

The active fragments of the invention may be used in a method for treating cancer comprising administering at least one active fragment of CRMP-1 to a patient in need thereof and allowing the active fragment(s) to inhibit the proliferation, metastasis, and/or invasion of the cancer cells. The proliferation inhibition effect of certain CRMP-1 fragments was shown in colon, breast, lung, and prostate cancer cell lines. Specifically, at least one fragment demonstrated activity in each of the cell line.

The result indicates that the hCRMP-1 fragments are highly selective and could be applied as therapeutic agents with the expectation of low side effects. Additionally, certain cell fragments show better and broader inhibition effects to cancer cell growth than the full-length CRMP-1. Thus, while it is expected that the fragments will inhibit multiple types of cancer in different tissue types, it has presently been demonstrated that cancers of the colon, breast, lung, and prostate can be inhibited by at least one fragment of the invention. More specifically, at least one fragment inhibits lung adenocarcinoma, lung squamous cell carcinoma, lung large-cell carcinoma, prostate adenocarcinoma, prostate carcinoma, colon adenocarcinoma, and breast ductal carcinoma.

In certain embodiments, the patient is a mammal, and in other embodiments human. Veterinary treatment methods are also contemplated and include farm animals, such as horses, cows, pigs, family pets, such as dogs or cats, and other animals including non-human primates, rats, and mice.

Yet further, the present invention concerns the use of a combination of active CRMP-1 fragments with at least one chemotherapeutic agent. Administration of these active fragments substantially concurrently enhances the effectiveness of the chemotherapeutic agent(s). This may, in some embodiments, advantageously increase the chemosensitivity of cancer cells and thus allow for lower doses of these chemotherapeutic agents. This can also substantially reduce unwanted and problematic side effects.

Chemotherapeutic agents include COX-2 inhibitors such as caffeic acid phenethyl ester (CAPE), cell cycle-specific antibiotics such as Adriamycin™ (doxorubicin), and cell cycle G2 phase-specific drugs such as paclitaxel. Alternative chemotherapeutic agents include alkylating agents such as cisplatin, carboplatin, cyclophosphamide, and oxaliplatin; anti-metabolites such as azathioprine, 5-fluorouracil; plant alkaloids and terpenoids such as vinca alkaloids and podophyllotoxin; and type I and II topoisomerase inhibitors such as camptothecins, etoposide, and teniposide. Additionally, mixtures of these agents may be used.

Substantially concurrently includes administration of the fragments prior to, concurrently with, or subsequent to the administration of a chemotherapy agent. It includes treatments that are 1 minute apart, 2 minutes apart, 3 minutes apart, 4 minutes apart, 5 minutes apart, 10 minutes apart, 20 minutes apart, 30 minutes apart, 1 hour apart, 2 hours apart, 1 day apart, 2 days apart, or are included in the same treatment cycle.

B. Formulation and Routes of Administration

One embodiment of the present invention relates to a pharmaceutical composition comprising at least one active fragment of CRMP-1 and at least one pharmaceutically acceptable carrier.

Depending on the particular cancer to be treated, administration of pharmaceutical compositions according to the present invention will be via any common route so long as the target tissue is available via that route. This includes oral, nasal, buccal, rectal, vaginal or topical. Topical administration would be particularly advantageous for treatment of skin cancers. Alternatively, administration will be by orthotopic, intradermal, subcutaneous, intramuscular, intraperitoneal or intravenous injection. Such compositions would normally be administered as pharmaceutically acceptable compositions that include physiologically acceptable carriers, buffers or other excipients.

In certain embodiments, pharmaceutical formulations will include active fragment(s) of CRMP-1 in combination with a pharmaceutically acceptable vehicle, such as saline, buffered saline, 5% dextrose in water or the like. Formulations may further include one or more excipients, preservatives, solubilizers, buffering agents, albumin to prevent nonspecific binding, extend half-life, etc. The CRMP-1 fragment and an additional anticancer drug may be administered separately or in combination as a single composition. Thus, the formulations may be provided as a single formulation or as a multicomponent kit. Methods of formulation are well known in the art and are disclosed, for example, in Remington's Pharmaceutical Sciences, Gennaro, ed., Mack Publishing Co., Easton Pa., 1990, which is incorporated herein by reference.

Where clinical application of a composition is contemplated, it will be necessary to prepare the pharmaceutical composition appropriate for the intended application. Generally this will entail preparing a pharmaceutical composition that is essentially free of impurities that could be harmful to humans or animals. One also will generally desire to employ appropriate salts and buffers to render the pharmaceutical composition stable and allow for uptake by target cells.

In a further embodiment of the present invention, the active fragments may be used with a time-release means such as, for example, liposomes and polysaccharides for effecting continual dosing of said fragments. Time-release formulations generally include a monolithic delivery device comprising biocompatible solutions, gels, pastes, and putties in a matrix, in which the composition is entrapped or dissolved. Release from such a timed-release composition occurs by diffusion through the matrix and/or erosion of the matrix. A reservoir system, where the pharmaceutical composition diffuses through a membrane, may also be used.

In certain embodiments, ex vivo therapies also are contemplated. Ex vivo therapies involve the removal, from a patient, of target cells. The cells are treated outside the patient's body and then returned. One example of ex vivo therapy would involve a variation of autologous bone marrow transplant. Many times, ABMT fails because some cancer cells are present in the withdrawn bone marrow, and return of the bone marrow to the treated patient results in repopulation of the patient with cancer cells. In one embodiment, however, the withdrawn bone marrow cells could be treated while outside the patient with a viral particle that targets and kills the cancer cell. Once the bone marrow cells are "purged," they can be reintroduced into the patient. Such an embodiment would be beneficial for cancers of the blood.

C. Dosage Amount and Frequency

Physicians skilled in the art would be able to dose the active fragments of the invention, as well as any contemplated combination therapy, designing both dosage amounts and dosage frequency.

The effective amount refers to an amount of the composition that is capable of producing a medically desirable result in a treated subject. Take tumor treatment as an example, compared to an untreated subject, the desirable result comprises the inhibition of proliferation, metastasis, and/or invasion, and may decrease of tumor mass, growth rate, metastasis, alleviation of symptoms, extension of life, and/or improvement of life quality. The exact dosage for administration depends on the types, extent or symptom of the disease, as well as the health conditions, age, sex, weight, or drug toleration of the subject to be administered. The amount for administration also varies with the extent, severity, and type of tumor. One skilled in the art can decide the suitable dosage for administration according the foregoing or other factors.

The treatments may include various "unit doses." Unit dose is defined as containing a predetermined-quantity of the therapeutic composition calculated to produce the desired responses in association with its administration, i.e., the appropriate route and treatment regimen. The quantity to be administered, and the particular route and formulation, are within the skill of those in the clinical arts. Also of import is the subject to be treated, in particular, the state of the subject and the protection desired. A unit dose need not be administered as a single injection but may comprise continuous infusion over a set period of time.

Generally, compositions of the present invention are administered to a patient at a dose ranging from about 1 µg/kg to about 20 mg/kg, about 1 µg/kg to about 10 mg/kg, about 1 µg/kg to about 1 mg/kg, about 10 µg/kg to about 100 µg/kg, about 10 µg/kg to about 1 mg/kg, about 100 µg/kg to about 1 mg/kg, about 100 µg/kg to about 10 mg/kg, or about 200 µg/kg to about 1 mg/kg. For example, compositions of the present invention can be administered at a dose ranging from about 80 µg to about 1600 mg, about 80 µg to about 800 mg, about 80 µg to about 80 mg, about 800 µg to about 8 mg, about 800 µg to about 80 mg, about 8 mg to about 80 mg, about 8 mg to about 800 mg, or about 16 mg to about 80 mg. In another example, compositions of the present invention can be administered at a dose ranging from about 50 µg to about 1000 mg, about 50 µg to about 500 mg, about 50 µg to about 50 mg, about 500 µg to about 5 mg, about 500 µg to about 50 mg, about 5 mg to about 50 mg, or about 5 mg to about 500 mg, or about 10 mg to about 50 mg.

IV. Methods of Using the Nucleic Acid Sequences Encoding the Active Fragments of CRMP-1

One aspect of the present invention relates to an expression vector that can be a "plasmid," which includes a circular double stranded DNA into which additional DNA segments can be introduced.

The expression vectors of the present invention comprise a polynucleotide encoding active fragments of CRMP-1. The expression vectors also include one or more regulatory sequences operably linked to the polynucleotide being expressed. These regulatory sequences are selected based on the type of host cell used. It will be appreciated by those skilled in the art that the design of the expression vector depends on such factors as the choice of the host cells and the desired expression levels.

In one embodiment, the expression vector contains tissue-specific regulatory elements. Examples of suitable tissue-specific promoters include the liver-specific albumin promoter, lymphoid-specific promoters, promoters of T cell receptors and immunoglobulins, neuron-specific promoters (e.g., the neurofilament promoter), pancreas-specific promoters, mammary gland-specific promoters (e.g., milk whey promoter), and tumor specific promoters.

In another embodiment, the expression vector contains a regulatable expression system. Systems suitable for this invention include, but are not limited to, the Tet-on/off system (Gossen et al., *Science* 268: 1766-1769 (1995); Kistner et al., *Proc. Natl. Acad. Sci. USA.* 93: 10933-10938 (1996)), the Ecdysone system (No et al., *Proc. Natl. Acad. Sci. USA.* 93: 3346-3351 (1996)), the Progesterone-system (Wang et al, *Proc. Natl. Acad. Sci. USA.* 93: 8180-8184 (1994); Wang et al., *Nat. Biotech.* 15: 239-243 (1997)), and the Rapamycin system (Magari et al., *J. Clin. Invest.* 100: 2865-2872 (1997); Ye et al., *Science* 283: 88-91 (1999)).

Several specific vectors are further contemplated as embodiments of this invention. In one embodiment, the expression vector is a viral vector. Examples of the viral vectors include, but are not limited to, retroviral, lentiviral, adenoviral, adeno-associated viral (AAV), herpes viral, or alphavirus vectors. The viral vectors can also be astrovirus, coronavirus, orthomyxovirus, papovavirus, paramyxovirus, parvovirus, picornavirus, poxvirus, or togavirus viral vectors.

In certain embodiments, an ATG may be added to the nucleic acids encoding active fragment to ensure proper reading frame and proper expression.

V. Methods of Inhibiting Proliferation Using Full-Length or Substantially Full-Length CRMP-1

It has now surprisingly been discovered that full-length CRMP-1 inhibits proliferation of cancer cells, when it was previously shown not to have this effect in lung cancer cells. Previously, it was believed that CRMP-1 inhibited cancer only by inhibiting invasion and metastasis. Specifically, recent work reported that the expression of CRMP-1 inhibits invasion and metastasis of lung cancer cells (Shih et al., *J. Natl. Cancer Inst.* 93(18): 1392-1400 (2001)). Further, the prior art suggested that CRMP-1 did not inhibit cell proliferation. In fact, Shih et al. determined that hCRMP-1 did not affect the proliferation of cancer cells in a panel of poorly differentiated adenocarcinoma lung cancer cell lines established from a patient.

It is therefore surprising to disclose that the full-length hCRMP-1 inhibits cancer cell proliferation, as well as the invasive activity and metastasis, in two prostate cancer cell lines (PC-3 and DU145), colon cancer cell line CC-M1, breast cancer cell line MCF-7, and human lung large-cell carcinoma cell H460.

Therefore, in one aspect of this invention, full-length or substantially full-length CRMP-1 is used to inhibit proliferation of cancer. In another embodiment, CRMP-1 is used to inhibit proliferation of lung cancer, including human squamous lung cancer, adenocarcinoma carcinoma, and large-cell carcinoma; prostate cancer, including adenocarcinoma and carcinoma, colon cancer, including adenocarcinoma, and breast cancer, including ductal carcinoma. Investigating the growth characteristics of malignant cells overexpressing hCRMP-1.

It will be recognized that the above discussion regarding amino acid and nucleic acid variants, methods of treatment, formulation and routes of administration, dosage amount and frequency and nucleic acid expression apply equally to methods of using full-length or substantially full-length CRMP-1 as to the fragments discussed above, with the exception that it is intent of the invention to focus on inhibiting proliferation with full-length or substantially full-length CRMP-1, whereas the inventive methods of using the fragments encompass proliferation, metastasis, and/or invasion.

Definitions

The term "activity", as used herein, refers to any biological property of CRMP-1 and its fragments. The activity may, for example, be inhibiting proliferation, metastasis, and/or invasion in response to treatment. Such activity may be determined by standard assays in the art for proliferation, metastasis, and/or invasion.

As used herein the term "cell proliferation": is defined as the reproduction or multiplication of cells.

As used herein the term "effective amount" is defined as an amount of the agent that will inhibit proliferation, metastasis, and/or invasion of the cancer. For example, it may decrease, reduce, inhibit or otherwise abrogate the growth of a cancer cell, induce apoptosis, inhibit angiogenesis of a tumor cell, inhibit metastasis, or induce cytotoxicity in cells. Thus, an effective amount is an amount sufficient to detectably and repeatedly ameliorate, reduce, minimize or limit the extent of the disease or its symptoms. More rigorous definitions may apply, including elimination, eradication or cure of disease.

The term "gene" as used herein, refers to a polymer in which nucleotides encoding the amino acids constituting a polypeptide (e.g., enzyme) are joined into a linear structure with directionality. The "gene" may be single-stranded (e.g., RNA) or double-stranded (e.g., DNA). DNA may be, for example, cDNA which is enzymatically prepared from a transcribed RNA (mRNA), genomic DNA from chromosomes, or chemically synthesized DNA.

"Homology" is generally determined using a sequence-analysis software package (for example, Sequence Analysis Software Package of the Genetics Computer Group, University of Wisconsin Biotechnology Center, 1710 University Avenue, Madison, Wis. 53705). Similar amino acid sequences are aligned, in order to obtain the maximum degree of homology (i.e., identity or similarity, as defined above). For this purpose, it may be necessary to introduce gaps into the sequence artificially. Once the optimal alignment has been produced, the degree of homology is established by recording all of the positions for which the amino acids of the two compared sequences are identical, in relation to the total number of positions.

"Invasiveness" is the degree to which an organism such as cancer cell is able to spread through the body from one region such as the original site of tumor.

An "isolated," "purified," "substantially isolated," or "substantially pure" molecule (such as a polypeptide or polynucleotide) is one that has been manipulated to exist in a higher concentration than in nature. For example, a subject protein is isolated, purified, substantially isolated, or substantially purified when at least 50%, 70%, 75%, 80%, 85%, 90%, 91%, 92%, 93%, 94%, 95%, 96%, 97%, 98%, 99% or more of non-subject-protein materials with which it is associated in nature have been removed. As used herein, an "isolated," "purified," "substantially isolated," or "substantially purified" molecule includes recombinant molecules.

"Metastasis" is the process by which cancer spreads from the place at which it first arose as a primary tumor to distant locations in the body. Metastasis depends on the cancer cells acquiring two separate abilities—increased motility and invasiveness. Cells that metastasize are basically of the same kind as those in the original tumor. If a cancer arises in the lung and metastasizes to the liver, the cancer cells in the liver are lung cancer cells. However, the cells have acquired increased motility and the ability to invade another organ.

The term "nucleic acid sequence", as used herein, refers to a DNA, cDNA or RNA molecule, either as a separate fragment or as part of a larger polynucleotide construct.

The terms "patient," "subject," "individual," and "host" are used interchangeably herein to refer to a living animal, including a human and a non-human animal. The subject may, for example, be an organism possessing immune cells capable of responding to antigenic stimulation, and stimulatory and inhibitory signal transduction through cell surface receptor binding. The subject may be a mammal, such as a human or non-human mammal, for example, farm animals, such as horses, cows, pigs, family pets, such as dogs or cats, and other animals including non-human primates, rats, and mice. The term "subject" does not preclude individuals that are entirely normal with respect to a disease, or normal in all respects.

The expression vector can be a "plasmid," which includes a circular double stranded DNA into which additional DNA segments can be introduced. Other forms of vectors include expression vectors and gene delivery vectors.

In general, the term "protein" refers to any polymer of two or more individual amino acids (whether or not naturally occurring) linked via peptide bonds, as occur when the carboxyl carbon atom of the carboxylic acid group bonded to the α-carbon of one amino acid (or amino acid residue) becomes covalently bound to the amino nitrogen atom of the amino group bonded to the α-carbon of an adjacent amino acid. These peptide bond linkages, and the atoms comprising them (i.e., α-carbon atoms, carboxyl carbon atoms (and their substituent oxygen atoms), and amino nitrogen atoms (and their substituent hydrogen atoms)) form the "polypeptide backbone" of the protein. In addition, as used herein, the term "protein" is understood to include the terms "polypeptide" and "peptide" (which, at times, may be used interchangeably herein). Similarly, protein fragments, analogs, derivatives, and variants are may be referred to herein as "proteins," and shall be deemed to be a "protein" unless otherwise indicated. The term "fragment" of a protein refers to a polypeptide comprising fewer than all of the amino acid residues of the protein. As may be appreciated, a "fragment" of a protein may be a form of the protein truncated at the amino terminus, the carboxy terminus, and/or internally (such as by natural splicing), and may also be variant and/or derivative. A "domain" of a protein is also a fragment, and comprises the amino acid residues of the protein required to confer biochemical activity corresponding to naturally occurring protein.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide.

The term "stringent conditions", as used herein, is the "stringency" which occurs within a range from about Tm-5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences. Stringent conditions include, for example, 0.5 M NaHPO$_4$, 7% sodium dodecyl sulfate (SDS), 1 mM EDTA at 65° C., and washing in 0.2×SSC/0.1% SDS at 42° C. (see Ausubel, et al (eds), 1989, Current Protocols in Molecular Biology, Vol. 1, Green Publishing Associates, Inc., and John Wiley & Sons, Inc., New York, at p. 2.10.3). Alternatively, stringent conditions may, for example, include 0.5 M NaHPO$_4$, 7% SDS, 1 mM EDTA at 65° C., and washing in 0.1×SSC/0.1% SDS at 68° C. (see Ausubel, et al (eds), 1989, Current Protocols in Molecular Biology, Vol. 1, Green Publishing Associates, Inc., and John Wiley & Sons, Inc., New York, at p. 2.10.3).

The term "treatment" refers to a therapeutic or preventative measure. The treatment may be administered to a subject having a medical disorder or who ultimately may acquire the disorder, in order to prevent, cure, delay, reduce the severity of, or ameliorate one or more symptoms of a disorder or recurring disorder, or in order to prolong the survival of a subject beyond that expected in the absence of such treatment.

The term "variant" refers to proteins, peptides, nucleic acids, and fragments thereof that differ from the original CRMP-1, fragments of CRMP-1, and nucleic acid encoding CRMP-1 and fragments of CRMP-1 by one or more substitutions, deletions, and/or insertions. In some embodiments, these modifications generally do not substantially change (e.g., reduce or enhance) the original biological function. However, in other instances, a variant of CRMP-1 fragment can reduce or enhance the biological activities of the original fragment, while still being useful in the invention.

Polypeptide variants include those conservative substitutions, which are substitutions of amino acids of the same category, such as substitutions of amino acids with non-charged side-chains (such as asparagine, glutamine, serine, threonine and tyrosine), of amino acids with basic side-chains (such as lysine, arginine and histidine), of amino acids with acid side-chains (such as aspartic acid and glutamic acid), and of amino acids with apolar side-chains (such as glycine, alanine, valine, leucine, isoleucine, proline, phenylalanine, methionine, tryptophan and cysteine). Additionally, variants include substitution of natural amino acids with unnatural amino acids or pseudo amino acids, in positions such that these modifications do not significantly impair the biological activity of the hCRMP-1 or active fragments thereof.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

EXAMPLES

Example 1

Construction of Expression Plasmid pNCRMP1

A) Preparation of cDNA from Human Lung Adenocarcinoma Cell Line CL$_{1-0}$

Total RNA was extracted from 1×10$^7$ human lung adenocarcinoma cells, CL$_{1-0}$, using the phenol-based method (TRIzol reagent, Texas, USA). The cDNA was reverse transcribed from 0.005 mg total RNA and by using SuperScript II Reverse Transcriptase (Invitrogen, USA) according to the protocol from manufacturer.

B) Amplification of hCRMP-1 Gene Fragment

The amino acid sequences and cDNA sequence of hCRMP1 is listed in SEQ ID NO: 1 and 2, respectively. A 1.8 kb DNA fragment containing nucleotides from +142 to +1866 of human collapsin response mediator protein-1 (hCRMP-1) gene (GenBank Accession No. D78012, NCBI) was obtained by PCR amplification using two primers:

(1) NeocF, as forward primer, 5'-GATTCTCGAGGGGG CCATGTCGTACCAGGGCAAG-3' (SEQ ID NO:3, position +142 to +168, with an additional, artificial XhoI site (italic) at the 5'-end); and (2) NeocR, as reverse primer, 5'-GTCTAGArCAgtgatggtg-gtggtgatg ACCGAGGCTGGTGATG-3' (SEQ ID NO:4, sequence complementary to position +1866 to +1851, with an additional, artificial XbaI site (italic), 6×His tag (SEQ ID NO: 44) (lowercase), and the stop-codon (bold) at the 5'-end).

C) Construction of pNCRMP1 Expression Plasmid

The amplified product was purified from PCR mixture, digested with XhoI and XbaI restriction endonucleases, and inserted into the linear pCI-neo Mammalian Expression Vector (Promega, USA) restricted with XhoI and XbaI enzymes. This construct was designated as pNCRMP1. The translated amino acid sequence of the inserted fragment showed 100% homology to the published sequence (Hamajima et al., *Gene* 180: 157-163 (1996)), but with one single nucleotide polymorphism (SNP; refSNP ID: rs12331). The pCI-neo Mammalian Expression Vector is a selectable vector for studying constitutive expression of cloned gene in mammalian cells.

Example 2

Construction of a Series of Expression Plasmid Containing Partial hCRMP-1 Gene Fragment Six partial DNA fragments of hCRMP1 gene obtained by PCR amplification using pNCRMP1 as DNA template and inserted into the commercial available pCI-neo Mammalian Expression Vector (Promega, USA). They were named as pNCN1, pNCN3, pNCN4, pNCN5, pNCN6, and pNCN7, respectively. Related information for the amplification of partial hCRMP-1 gene fragments were listed in Tables 3-5, including the primer pairs, nucleotide sequence of each primer, and the coverage of amino acid sequence range of individual partial fragment of hCRMP-1 gene. Table 5 provides both the amino acid sequences and the cDNA sequences of CRMP-1 fragments constructed. Some CRMP-1 fragments contain one additional methionine (represented as symbol "M" in amino acid sequence listings) in the expression construct in order to build an "open reading frame" and can be expressed as protein in mammalian cells or in prokaryote cell (e.g. *E. coli*).

TABLE 3

PCR AMPLIFICATION-RELATED INFORMATION FOR CONSTRUCTION OF EXPRESSION PLASMIDS

| Plasmid ID | Forward primer | Reverse primer |
|---|---|---|
| pNCN1 | CN1-F | CNR |
| pNCN3 | CN3-F | CNR |
| pNCN4 | CN4-F | CNR |
| pNCN5 | CN5-F | CN5-R |
| pNCN6 | CN6-F | CN6-R |
| pNCN7 | CN7-F | CN7-R |

An additional start-codon sequence (ATG, shaded) was designed in forward primers, such as CN3-F, CN4-F, CN5-F, CN6-F, and CN7-F, in order to have the right translational start for gene reading frame during expression in mammalian cells (Table 4). Three forward primers, CN1-F, CN3-F, and CN4-F, have an additional, artificial XhoI (italic) site at the 5'-end, while the CNR reverse primer has an additional and artificial XbaI (italic) site and the stop-codon (bold) at the 5'-end. The other three forward primers, CN5-F, CN6-F, and CN7-F, have an additional and artificial SalI (italic) site at the 5'-end, while the reverse primers, CN5-R, CN6-R, and CN7-R, have an artificial NotI (italic) site, 6×His tag (SEQ ID NO: 44) (lowercase) and the stop-codon (bold) at the 5'-end.

The amplified DNA fragments for construction of pNCN1, pNCN3, and pNCN4 plasmid were first digested with restriction endonucleases XhoI and XbaI, respectively, while construction of other plasmids, such as pNCN5, pNCN6, and pNCN7, was with restriction endonucleases SalI and NotI. The restricted DNA fragments were ligated into pCI-neo vector predigested with the respective restriction enzymes.

TABLE 4

SEQUENCE LIST OF AMPLIFICATION PRIMERS

| Primer ID | Sequence (5'-3') | SEQ ID NO |
|---|---|---|
| CN1-F | ACTCGAGGCCATGTCGTACCAGGGCAAGAAG | 5 |
| CN3-F | CTCGAGACCATGGAACAAAAGCGGATCCTGG | 6 |
| CN4-F | CTCGAGACCATGGACTACTTGACCTCCCTAC | 7 |
| CNR | TTCTAGACTACTGGTACAGGTGCTCCGGG | 8 |
| CN5-F | GAATACTCATACTCTTCCGGATCCGTCGACGCCACCATGGTGCTGGTGCAGGACAAAGG | 9 |
| CN6-F | GAATACTCATACTCTTCCGGATCCGTCGACGCCACCATGATAGCTCAGGAACAAAAG | 10 |
| CN7-F | GAATACTCATACTCTTCCGGATCCGTCGACGCCACCATGAACATCAACGTCAACAAGG | 11 |
| CN5-R | CAGCGGCCGCTCAgtggtggtgatggtggtgGTCGGCTGCACTCTTGCTC | 12 |
| CN6-R | TAGCGGCCGCTCAgtgatgatggtgatgatgTAGGGAGGTCAAGTAGTCG | 13 |
| CN7-R | TAGCGGCCGCTCAgtgatgatggtgatgatgACCGAGGCTGGTGATGTTGG | 14 |

Reference sequence: GenBank Accession No. D78012, NCBI

TABLE 5

AMINO ACID SEQUENCES OF PARTIAL DOMAINS CORRESPONDING THE AMPLIFIED DNA FRAGMENT OF HCRMP-1

| ID of Partial domain | Plasmid ID | Sequence range covered* | SEQ ID NO (AA, cDNA) |
|---|---|---|---|
| CN1 | pNCN1 | 1 to 480 | 15, 16 |
| CN3 | pNCN3 | 208 to 480 | 17, 18 |
| CN4 | pNCN4 | 315 to 480 | 19, 20 |
| CN5 | pNCN5 | 154 to 262 | 21, 22 |
| CN6 | pNCN6 | 205 to 320 | 23, 24 |
| CN7 | pNCN7 | 458 to 572 | 25, 26 |

*Sequence positions were based on the published sequence GenBank Accession No. BAA11190.

Example 3

Antiproliferative Effect on Mammalian Cells Transfected with Expression Plasmids, pNCRMP1, pNCN3, pNCN4, pNCN5, pNCN6, and pNCN7

A) Materials and Methods
1. Cell Lines and Cultivation Conditions

All cell lines were purchased from Food Industry Research and Development Institute (FIRDI), Hsinshu, Taiwan. They were originated from different tissues or organs, including:

(1) human lung cancer cells: adenocarcinoma A549 (BCRC60074), squamous cell carcinoma H520 (BCRC60124), and large-cell carcinoma H460 (CCRC600373), (2) human prostate cancer cell: adenocarcinoma PC-3 (CCRC60112) and carcinoma DU145 (CCRC60348) isolated from metastatic brain site;

(3) human colon cancer cells: adenocarcinoma SW 480 (CCRC60249), CC-M1 (BCRC60448), and DLD-1 (CCRC60132);

(4) human breast cancer cells: ductal carcinoma BT-474 (CCRC 60359), MCF-7 (CCRC60436), and ZR-75-1 (CCRC60055);
(5) Chinese hamster lung cell V79-4 (BCRC60183), and
(6) human prostate normal cell PZ-HPV-7 (CCRC60136).

overexpressed corresponding to the partial domain of hCRMP-1, named as CN1, CN3, CN4, CN5, CN6, and CN7 domain, respectively. Table 6 represents the antiproliferative effect on cancer cells transfected with different expression plasmid.

TABLE 6

ANTI-PROLIFERATION EFFECT (IN PERCENTAGE, %) OF INDIVIDUAL CELL LINE AFTER TRANSIENT TRANSFECTION OF EXPRESSION PLASMID

| | Lung Cells | | | | Prostate Cells | | | Colon | | | Breast | | |
|---|---|---|---|---|---|---|---|---|---|---|---|---|---|
| | Cancer Cells | | | Epithelium Cells | Cancer Cells | | Epithelium Cells | Adenocarcinoma Cells | | | Carcinoma Cells | | |
| Plasmid | A549 | H460 | H520 | V79-4 | PC-3 | DU145 | PZ-HPV-7 | CC-M1 | DLD-1 | SW480 | BT474 | MCF-7 | ZR-75-1 |
| pNCRMP1 | −36 | 19 | 0 | 81 | 56 | 57 | 48 | 94 | 39 | ND | 1 | 72 | 26 |
| pNCN1 | −33 | 3 | 15 | ND | ND*[2] | ND | −44 | ND | ND | ND | ND | ND | ND |
| pNCN3 | −6 | 6 | 22 | 85 | 54 | 52 | 30 | 93 | 52 | 6 | −97 | 75 | 17 |
| pNCN4 | 10 | −5 | 31 | ND | −3 | 7 | 14 | ND | ND | ND | ND | ND | ND |
| pNCN5 | −26 | ND | 34 | −7 | −3 | −45 | −17 | 40 | 25 | 0 | −31 | 25 | −13 |
| pNCN6 | −17 | ND | 2 | −8 | −4 | 46 | 50 | 29 | 14 | −14 | ND | 43 | −5 |
| pNCN7 | −10 | ND | 44 | −5 | 11 | 28 | −34 | 8 | 19 | 0 | −43 | 33 | −15 |

ND: no determination

The cultivation of cell lines was as described as the instruction provided by Food Industry Research and Development Institute (FIRDI), while 10% fetal bovine serum (JRH Biosciences, USA) was supplemented as final concentration, if necessary. The human prostate normal cell line PZ-HPV-7 was maintained in Keratinocyte-SFM medium (Life Technologies, Inc., US).

2. Transient Transfection

Mammalian cells were seeded to 6-well plate (Corning Inc., USA) with a cell density of $2\sim8\times10^5$ and incubated at 37° C. for overnight prior to transfection. Each cell line was respectively transfected with the pCI-neo Mammalian Expression Vector (as control plasmid; Promega, USA) or with the hCRMP-1-related expression plasmid by using Lipofectamine™ Reagent (Invitrogen, #18324-020). A series of expression plasmid containing full-length or partial gene fragment of hCRMP-1, were pNCRMP1, pNCN1, pNCN3, pNCN4, pNCN5, pNCN6, and pNCN7, whose constructions were described in Example 1 and Example 2.

The nomenclature of transfected cell line was according to the cell line and expression plasmid and characterized as "cell line/expression plasmid." Quantitation of viable cells after transfection was performed by using hemocytometer after 5-days incubation at 37° C. (R. Ian Freshney: Culture of Animal Cells, A Manual of Basic Technique, Chapter 20, pp. 309-312, WILEY-LISS, Canada (2000)).

The antiproliferative effect (in percentage) of each cell line transfected with individual expression plasmid was normalized with the same cell line transfected with control plasmid as follows:

Antiproliferative effect=100%×(1−(number of cells transfected with expression plasmid÷number of cells transfected with control plasmid))

B) Results

The full-length hCRMP-1 was expected to constitutively overexpress in the indicated cell line transfected with pNCRMP1 plasmid. The transfection of a series of expression plasmid in indicated cells, including pNCN1, pNCN3, pNCN4, pNCN5, pNCN6, and pNCN7, represented to have 1. Antiproliferative Effect on Prostate Cells after Transient Transfection The growth of both prostate cancer cell lines (PC-3 and DU145) transfected with pNCRMP1 or pNCN3 showed to be significantly, above 50%, inhibited. The proliferation of the transfected cells, DU145/pNCN6 and DU145/pNCN7, was inhibited up to 46% and 28%, respectively. It indicates that the overexpression of full-length hCRMP-1 protein or its partial domains, such as CN3, CN6, and CN7, in prostate cancer cells could effectively suppress cell growth. Specifically, the overexpressed CN3 domain in the human prostate cancer cell lines, such as PC-3 and DU145, showed to have around 20% more selectivity on antiproliferative ability than in the CN3-overexpressing human prostate normal cell line PZ-HPV-7. The CN7-overexpressing DU145 cells achieved better, with 28% selectivity of inhibition than the CN3-overexpressing cells, though the CN7 domain resulted in overall lower antiproliferative effect. The advantage of using CN3 or CN7 domain as treatment agent for tumor suppression will expectedly reduce side effects regarding the selectivity.

2. Antiproliferative Effect on Lung Cancer Cells after Transient Transfection

The proliferation of the human squamous lung cancer cells (H520) was inhibited ranging from 15% to 44% after transient transfection with expression plasmid pNCN1, pNCN3, pNCN4, pNCN5, and pNCN7, respectively. The antiproliferative effect on the transfectant H520/pNCN7 was the most significant than the on other H520 transfectants. The introduction of pNCN5 or pNCN7 plasmid into the H520 cells showed furthermore a better selectivity, 34% and 44%, respectively, since the cell growth of Chinese hamster lung transfectant cell, V79-4/pNCN5 and V79-4/pNCN7, was not affected. The application of high selective agents for administering gives the advantage to reduce side effects or bring the synergetic or additional effect by combinational approach without additional toxic effect on normal cells.

The antiproliferative effect on the other lung cancer cells, such as adenocarcinoma carcinoma cells (A549) and large-cell carcinoma cells (H460), after transient transfection with expression plasmid was varying. Only the transfectant A549/pNCN4 showed the slightly inhibited proliferation, but not the transfectant with other expression plasmids. Around 19% and 6% reduction of proliferation ability of large-cell carcinoma cells (H460) was measured for the transfectants with pNCRMP1 and pNCN3, respectively.

3. Antiproliferative Effect on Colon Cancer Cells after Transient Transfection

The cell growth of three colon cancer cell lines, CC-M1, DLD-1, and SW480, after individual transient transfection with pNCRMP1, pNCN3, pNCN5, pNCN6, and pNCN7, were studied. The relative antiproliferative effect on colon cancer cells was obtained after normalization with the effect on the same cell line transfected with control plasmid pCI-neo. The best inhibition on cancer cell growth, over 90%, was observed on the transfected cells, CC-M1/pNCRMP1 and CC-M1/pNCN3. The anti-proliferation effect on other CC-M1 transfectants, such as CC-M1/pNCN5 and CC-M1/pNCN6, achieved to 40% and 29%, respectively.

The cell growth of all colon cancer cell DLD-1 transfectants was more or less inhibited ranging from 14% to 52%, while the transfectant DLD-1/pNCN3 was the most affected. No effect on cell growth of the colon cancer cells SW480 could be observed.

4. Antiproliferative Effect on Breast Cancer Cells after Transient Transfection

Three breast cancer cell lines, BT-474, MCF-7, and ZR-75-1, were applied for transient transfection with pNCRMP1, pNCN3, pNCN5, pNCN6, and pNCN7. The measurement of living MCF-7 cells after transfection with pNCRMP1 and pNCN3 showed that the cell growth was significantly, over 70%, inhibited. The introduction of other expression plasmids, pNCN6, pNCN7, and pNCN5, resulted in the growth inhibition of MCF-7 cells with descending ratio ranging from 43% to 25%.

The proliferation of ZR-75-1 was slightly, 26% and 17%, affected after transient transfection with pNCRMP1 and pNCN3, respectively, but not with the other expression plasmids. No effect on cell growth of the breast cancer cell lines BT-474 could be observed.

Example 4

Focus Formation Assay of Cancer Cells Transfected with Expression Plasmid, pNCRMP1, pNCN3, pNCN5, pNCN6, and pNCN7

A) Material and Methods

The human lung squamous carcinoma cell line H520 and two human prostate cancer cell lines, PC-3 and DU145, were transfected with pNCRMP1, pNCN3, pNCN5, pNCN6, and pNCN7, while transfection of the same cells with pCI-neo vector served as control studies, respectively. The procedures for transient transfection were the same as described in Example 3.

The focus formation assay of transfected cells was performed as described as published by Bartholomeusz et al. (Cancer Research 65(18): 8406-8413 (2005)) with modifications. The cells after transfection process were incubated in fresh culture medium at 37° C. for 2-5 days, divided in a 1:3~1:6 dilution into 6-well plate and followed with incubation for 3 weeks in selected medium containing 0.5-0.9 mg antibiotic G418 per ml. Colonies were finally counted by the staining method with crystal violet (R. Ian Freshney, WILEY-LISS, Protocol 15.3; pages 235-236 (2000)).

The relative reduction of focus formation ability (in percentage) of each cell line transfected with expression plasmid was obtained after normalization with the same cell line transfected with control plasmid (pCI-neo vector) using the following formula:

Relative reduction of focus formation ability=100%× (1−(colony number of cells transfected with expression plasmid÷colony number of cells transfected with control plasmid))

B) Results

The change of colony formation ability of the human cancer cells, in which hCRMP-1 or its partial domain was overexpressed, was further studied. Table 7 shows the relative inhibition ratio on colony formation of the human lung squamous carcinoma cells H520 and two human prostate cancer cell lines PC-3 and DU145 after respective transfection of hCRMP-1 gene-related expression plasmid. The full-length hCRMP-1 protein or its partial proteins, CN3, CN5, CN6, and CN7, was constitutively overexpressed in the transfected cells.

1. Change of Colony Formation Ability of Prostate Cancer Cells After Transfection More than 50% reduction of the colony formation ability of the transfectants, such as DU145/pNCRMP1, DU145/pNCN3, and DU145/pNCN6, was achieved. The best inhibition effect, up to 67%, could be observed for the DU145/pNCN3 transfectant. In other words, the constitutive overexpressed CN3 domain drastically eliminated the colony forming ability of the prostate cancer cell line DU145. The DU145/pNCN7 transfectant showed to have loss of around 25% colony formation ability, while the DU145/pNCN5 transfectant did not show any change.

Around 30% reduction of colony formation ability was observed for PC-3/pNCRMP1 transfectant. The colony formation ability of other PC-3 transfectants, such as PC-3/pNCN3, PC-3/pNCN5, and PC-3/pNCN7, showed to be slightly (13-15%) affected.

2. Change of Colony Formation Ability of Lung Cancer Cells after Transfection

Around 30% of the colony formation ability of the H520/pNCN5 transfectant was restrained. It indicates that the overexpressed CN5 partial domain specifically cause the transformation of the human lung squamous carcinoma cells H520, but not the full-length hCRMP-1 protein or other partial domains, CN3 and CN7, in this study.

TABLE 7

RELATIVE INHIBITION EFFECT ON COLONY FORMATION (IN PERCENTAGE, %) OF INDIVIDUAL CANCER CELL TRANSFECTANT

|  | Lung Cancer Cells | Prostate Cancer Cells | |
| --- | --- | --- | --- |
| Plasmid | H520 | PC-3 | DU145 |
| pNCRMP1 | 2 | 32 | 50 |
| pNCN3 | −31 | 15 | 67 |
| pNCN5 | 30 | 13 | 4 |
| pNCN6 | ND | ND | 52 |
| pNCN7 | −33 | 13 | 26 |

ND: Not determination

Example 5

Anchorage-Independent Assay of Cancer Cells Transfected with Expression Plasmids pNCRMP1, pNCN1, pNCN3, and pNCN4

A) Material and Methods

The human lung cancer cell lines A549, H460, and H520 were transfected with the pCI-neo vector (as control) and four hCRMP-1 gene-related expression plasmids, pNCRMP1, pNCN1, pNCN3, and pNCN4, respectively. The transient transfection methods were the same as described in Example 3.

The anchorage-independent assay used in this study was performed as described by Freshney (Culture of Animal Cells, A Manual of Basic Technique, Chapter 20, pp. 200-202, WILEY-LISS, Canada (2000)) with following modifications. These transfected cells were incubated in refreshed and selected medium containing antibiotic G418 with the concentration of 0.5-0.9 mg/ml for 2-5 days at 37° C., and following with suspension in soft-agars with a density of 4,000~6,000 cells per well. The mixture of cell/soft-argarose was plated on of 24-well plate underlay with agarose for 4-8 weeks. Colonies grown in soft-agarose were observed using reversed microscope and counted, only when the diameter of colony was greater than 0.05 mm. The anchorage-independent assay for each transfectant was carried out in triplicate.

The relative inhibition effect on colony growth in soft-agarose due to overexpression of hCRMP-1 or its truncated forms was calculated as follows:

Relative inhibition effect=100%×(1−(colonies derived from cells transfected with expression plasmid÷colonies derived from transfected cells with control plasmid))

B) Results

Anchorage-independent growth in semi-solid agarose is one of the characteristics of transforming ability for transformed cells. The ability of suspended colony formation in soft-agarose system of three human lung cancer cell types after individual transfection with pNCRMP1, pNCN1, pNCN3, and pNCN4 plasmid, as well as the pCI-neo (as control plasmid), was studied.

The ability of suspended colony formation in soft-agarose of all three types of human lung cancer cell lines was considerably inhibited with the range from around 50% to 100% (Table 8). Both human large-cell carcinoma transfectants, H460/pNCN3 and H460/pNCN4, which had higher expression level of CN3 and CN4 domain, respectively, seemed to loss the ability to grow under the anchorage independent conditions. This ability of other two H460 transfectants, H460/pNCRMP1 and H460/pNCN1, was also inhibited up to 75%.

The most effective inhibition (over 80%) on the anchorage independence of human lung adenocarcinoma cells A549 was also due to transfection with pNCN4 plasmid. These results indicate that the CN4 partial domain plays the critical role for inhibition of colony formation in soft-agarose, especially for the adenocarcinoma and large-cell carcinoma type, but not squamous type.

As shown in Table 8, four (4) H520 transfected cell lines had lost almost half of the ability for anchorage-independent growth.

TABLE 8

RELATIVE INHIBITION OF COLONIES GROWTH (IN PERCENTAGE, %) IN SOFT-AGAROSE

| Plasmids | Lung Cancer | | |
|---|---|---|---|
| | A549 | H460 | H520 |
| pNCRMP1 | 62 | 75 | 46 |
| pNCN1 | 68 | 75 | 61 |
| pNCN3 | 75 | 100 | 58 |
| pNCN4 | 82 | 100 | 54 |

Example 6

Improvement of Chemosensitivity of Cancer Cells Using Combinational Approach

A) Material and Methods

1. Selection of Stable Transfectants with Overexpressed hCRMP-1 or its Partial Domains Three human cancer cell lines, including lung cancer cell line H520 and two human prostate cancer cell lines (PC-3 and DU145) were applied for selection of stable transfectants. Four expression plasmids, including pNCRMP1, pNCN1, pNCN3, and pNCN4, and the pCI-neo vector (as control plasmid) were used for transfection, respectively. The general cultivation condition and transfection procedures were the same as described in Example 3. The transfected cells were further cultivated under the same conditions as their parental cell lines and selected with 0.6-1 mg antibiotic G418 per ml (Kao et al., Oncogene 16: 546-554 (1998); Xiaolin et al, Cancer Research 65: 9762-9770 (2005)).

2. Treatment of Stable Transfectants with Chemical Agents

Three agents, including caffeic acid phenethyl ester (CAPE; Sigma, US), Adriamycin™ (doxorubicin) (Pharmacia & Upjohn S.P.A. Milan, Italy), and paclitaxel (Taxol; Bristol-Myers Squibb Co., Wallingford, Conn.), were dissolved in DMSO (dimethyl sulfoxide; Sigma) for preparation of stock solution, respectively. A serial dilution was prepared with DPBS buffer for chemosensitivity tests. The human lung squamous carcinoma stable transfectants H520 were treated with both CAPE and Adriamycin™ (doxorubicin) for four different concentrations, e.g. 0.05, 0.01, 0.002, and 0.0004 mM, while the administering of paclitaxel was performed at different concentrations, e.g. 1000, 200, 40, and 8 nM. Both types of prostate stable transfectants were only treated with paclitaxel for eight concentrations ranging from 0.1 mM to 1.28 nM with 1/5 dilution each step.

3. Cytotoxicity (Chemosensitivity) Assays

MTT (3-(4,5-dimethylthiazol-2-yl)-2,5-diphenyltetrazolium bromide; Sigma, Inc.) assay (Monks et al., J. Natl. Cancer Inst. 83:757-766 (1991); Paull et al, J. Natl. Cancer Inst. 81:1088-1092 (1989)) was applied for studying the cytotoxic effect of indicated agent. The absorbance was measured both at 545 nm and at 690 nm (served as reference) using the 96-well spectrophotometer reader (Emax, Molecular Device Inc., California, US) (Chen et al., Yi Xue Za Zhi (Taipei) 46:7-16 (1990)). The relative growth inhibition was calculated as follows:

Relative growth inhibition=100%×(1− $(OD_{545nm\ (Treated\ cells)} - OD_{690nm(Treated\ cells)}) \div (OD_{545nm(untreated\ cells)} - OD_{690nm(untreated\ cells)})$)

The 50% inhibition concentration ($IC_{50}$) was determined after graphical plotting of spectrophotometric measurements and interpolation by EXCEL software.

B) Results

Chemosensitivity of stable transfectants, with respect to three agents, caffeic acid phenethyl ester (CAPE), Adriamycin™ (doxorubicin), and paclitaxel, were studied, which represents a COX-2 inhibitor, a cell cycle-specific antibiotic, and a cell cycle G2 phase-specific drug, respectively. Table 9 shows the concentration of 50% inhibition ($IC_{50}$) of cell growth.

Stable transfectants were obtained after selection with prolong in antibiotic G418-containing media. The human lung squamous carcinoma H520 stable transfectant included H520/pCI-neo/1 (as control), H520/pNCRMP1/1, H520/pNCN1/1, H520/pNCN3/1, and H520/pNCN4/1. The prostate PC-3 stable transfectants were PC-3/pCI-neo/11-1 (as control), PC-3/pNCRMP1/1304, and PC-3/pNCN3/15-5.

1. Chemosensitivity of Stable Transfectants to Paclitaxel

The best improvement, up to 400-fold, of chemosensitivity could be observed on the prostate stable transfectant DU145/pNCRMP1/2 treated with paclitaxel. It is of great advantage to use sub-therapeutic concentrations of antineoplastic agent, which is much less toxic to normal cells.

None of stable prostate cancer cell DU145/pNCN3 derived from single colony could survive during the following extended antibiotic G418 selection. Those transient transfected cells with overexpressed CN3 domain were countable for growth inhibition assay, but could not be maintained for prolonged cultivation due to possible destruction of certain cellular functions. Therefore, the combinational treatment approach could not be performed for CN3-overexpressing stable DU145 cells.

No effect on chemosensitivity of both prostate stable transfectants, PC-3/pNCRMP1/1304 and PC-3/pNCN3/15-5, could be observed.

The combination of over-expression of CN3 or CN4 protein in the stable transfectants of the human lung squamous carcinoma H520 resulted in the increase of sensitivity to paclitaxel at least 4-fold.

TABLE 9

THE $IC_{50}$ (μM) OF OF CHEMICAL AGENTS FOR CANCER CELLS AFTER TREATMENT WITH STABLE TRANSFECTANTS

| Transfectant | CAPE | Adriamycin ™ (doxorubicin) | paclitaxel |
| --- | --- | --- | --- |
| H520/pCI-neo/1 | >50 | 0.74 | 0.031 |
| H520/pNCRMP1/1 | 17 | <0.4 | 0.012 |
| H520/pNCN1/1 | 23 | <0.4 | 0.012 |
| H520/pNCN3/1 | 29 | <0.4 | <0.008 |
| H520/pNCN4/1 | 27 | 0.5 | <0.008 |
| PZ-HPV-7 | ND | ND | 6.53 |
| DU145/pCI-neo/7 | ND | ND | 8 |
| DU145/pNCRMP1/2 | ND | ND | 0.02 |

ND: Not determined

2. Chemosensitivity of Stable Transfectants to Adriamycin™ (Doxorubicin)

The chemosensitivity of stable transfectants of the human lung squamous carcinoma H520 showed at least a 2-fold increase to Adriamycin™ (doxorubicin) after treatment with the full-length CMRP-1 or the CN3, CN4 fragment.

3. Chemosensitivity of Stable Transfectants to CAPE

The stable transfectant H520/pNCRMP1/1 showed at least a 3-fold increase in the chemosensitivity to CAPE after treatment with the full-length CMRP-1 or the CN3, CN4 fragment, while other stable transfectants were around 2-fold more sensitive.

These data suggest that the therapeutic effect of chemotherapeutic agents, including caffeic acid phenethyl ester (CAPE), Adriamycin™ (doxorubicin), and paclitaxel, could be improved by the introduction of hCRMP-1 gene-related expression plasmid before or during the chemotherapy.

C) Additional Experiment on Improvement of Chemosensitivity of Cancer Cells Using Transient Transfectants 1. Materials and Methods Six human cancer cell lines, including human colon cancer cell lines Caco-2, CC-M1, DLD-1; human prostate cancer cell lines DU145, PC-3; and human breast cancer cell line MCF-7, were tested in an experiment on improvement of chemosensitivity. Two expression plasmids, pNCRMP1 and pNCN3, and the pCI-neo vector (control plasmid), were used for transfection, respectively. The general cultivation conditions and transfection procedures were the same as described in Example 3.

Treatment of transient transfected cell lines using chemical agent was immediately performed as follows, and quantification of viable cells was performed by counting using hemocytometer after 3-days incubation at 37° C.:

(1) Three types of transient transfected human colorectal cancer cells were treated with 5-fluorouracil;

(2) The transient transfected human prostate cancer cell line DU145 was treated with Adriamycin™ (doxorubicin), cyclophosphamide and etoposide;

(3) The transient transfected human prostate cancer cell line PC3 was treated with cyclophosphamide, etoposide, and paclitaxel; and, (4) The transient transfected human breast cancer cell line MCF-7 was treated with Adriamycin™ (doxorubicin) and paclitaxel.

2. Results

Table 10 shows the concentration of 50% inhibition ($IC_{50}$) of cell growth. Both transient transfectants, MCF-7/pNCRMP1 and MCF-7/pNCN3, became much more chemosensitive to Adriamycin™ (doxorubicin). The values of $IC_{50}$ indicate that the combination approach can improve therapeutic effectiveness of Adriamycin™ (doxorubicin) up to 20-fold when the MCF-7 cell is transfected with pNCRMP1 and 6-fold with pNCN3.

The therapeutic effectiveness of paclitaxel can be improved up to 8-fold when the PC-3 cell is transient transfected with pNCN3 to paclitaxel. In contrast, as disclosed above, when using stable transfectant PC-3/pNCRMP1/1304 and PC-3/pNCN3/15-5 for treatment study, no improvement on therapeutic effectiveness of paclitaxel was observed.

When using 5-fluorouracil together with transient transfected colorectal cell lines, no improvement of chemosensitivity was observed (data not shown).

TABLE 10

THE $IC_{50}$ (μM) OF CHEMICAL AGENTS FOR CANCER CELLS AFTER TREATMENT WITH TRANSIENT TRANSFECTANTS

| | Agents* | | | |
| --- | --- | --- | --- | --- |
| Transfectant | Adriamycin ™ (doxorubicin) | Cyclophosphamide | Etoposide | Paclitaxel |
| DU145/pCIneo | 0.073 | >100 | 0.46 | ND |
| DU145/pNCRMP1 | 0.079 | >100 | 0.71 | ND |
| DU145/pNCN3 | 0.06 | >100 | 0.71 | ND |
| PC-3/pCIneo | ND | >100 | 64 | 0.087 |
| PC-3/pNCRMP1 | ND | >100 | 33 | 0.069 |
| PC-3/pNCN3 | ND | 55 | >100 | 0.01 |
| MCF-7/pCIneo | 2.13 | ND | ND | <0.001 |

TABLE 10-continued

THE IC$_{50}$ (μM) OF CHEMICAL AGENTS
FOR CANCER CELLS AFTER TREATMENT
WITH TRANSIENT TRANSFECTANTS

| | Agents* | | | |
|---|---|---|---|---|
| Transfectant | Adriamycin ™ (doxorubicin) | Cyclophos-phamide | Etoposide | Pacli-taxel |
| MCF-7/pNCRMP1 | 0.1 | ND | ND | <0.001 |
| MCF-7/pNCN3 | 0.32 | ND | ND | 0.044 |

ND: No determination
*Concentrations of agent:
Adriamycin ™ (doxorubicin) (in μM): 10, 1, 0.1, and 0.01
Cyclophosphamide and Etoposide (in μM): 100, 10, 0.1 and 0.01
Paclitaxel (in nM): 1000, 100, 10, and 1

Example 7

Plasmid Construction for Heterologous Expression of hCRMP-1 and its Domain (CN3) in *Escherichia coli*

A) Plasmid Construction for Heterologous Expression of hCRMP-1 in *Escherichia coli*

A 1716 bp-DNA fragment containing nucleotides from +151 to +1866 of human collapsin response mediator protein-1 (hCRMP-1) gene (GenBank Accession No. D78012) was obtained by PCR amplification using two primers:

(1) 2F, as forward primer, 5'-ATTGAAAGCTTATGTCG-TACCAGGGCA-3' (SEQ ID NO: 27, position +151 to +166, with an additional, artificial HindIII site (italic) at the 5'-end); and (2) 2R, as reverse primer, 5'-ATATCCTCGAGACCGAG-GCTGGTGATG-3' (SEQ ID NO: 28, sequence complementary to position +1866 to +1851, with an additional, artificial XhoI site (italic) at the 5'-end).

The amplified product was purified from PCR mixture using agarose gel elution and phenol/isopropanol extraction, digested with restriction endonucleases, HindIII and XhoI, and inserted into the HindIII/XhoI site of the pET-22b(+) plasmid (Novagen, USA). This construct was designated as pET22bCRMP1 and contains hCRMP-1 gene for coding the full-length protein with 572 amino acids (GenBank Accession No. BAA11190, NCBI). This pET system is widely used for the cloning and expression of recombinant proteins in *E. coli* under control of strong bacteriophage T7 transcription. The pET-22b(+) plasmid used in our study contains additional fragment encoding for 39 amino acids as signal peptide before the subcloned gene fragment.

B) Plasmid Construction for Heterologous Expression of CN3 Domain in *Escherichia coli*

An 820 bp-DNA fragment containing nucleotides from +772 to +1591 of human collapsin response mediator protein-1 (hCRMP-1) gene (GenBank Accession No. D78012, NCBI) was obtained by PCR amplification using two primers:

(1) CN3 PF, as forward primer, 5'-AGCAAGCTTGAA-CAAAAGCGGATCCTG-3' (SEQ ID NO: 29, position +772 to +789, with an additional, artificial HindIII site (italic) at the 5'-end); and (2) CNPR, as reverse primer, 5'-TAACTCGAGCTGGTA-CAGGTGCTCC-3' (SEQ ID NO: 30, sequence complementary to position +1591 to +1575, with an additional, artificial XhoI site (italic) at the 5'-end).

The amplified product was purified from PCR mixture using agarose gel elution and phenol/isopropanol extraction, digested with restriction endonucleases, HindIII and XhoI, and inserted into the HindIII/XhoI site of the pET-22b(+) plasmid (Novagen, USA). This construct was designated as pE22bCN3 and contains the coding region of amino acids from 208 to 480 of full-length hCRMP-1 (GenBank Accession No. BAA11190, NCBI).

Example 8

Production of Recombinant hCRMP-1 (rhCRMP-1) and its Partial Domain e-rCN3

A) Inducible Expression of Recombinant hCRMP-1 and its Partial Domain CN3 in *Escherichia coli*

Two expression plasmids, pET22bCRMP1 and pE22bCN3, were transformed into *Escherichia coli* strain BL21(DE3) according to Maniatis, et al. (Molecular Cloning: A Laboratory Manual, Cold Spring Harbor, (1989)), respectively. The transformant WJ4-1 (*E. coli* BL21 (DE3)/pET22bCRMP1) and WJ60-2 (*E. coli* BL21 (DE3)/pE22bCN3) with the highest production at the expected molecular weights for hCRMP-1 and e-rCN3, were selected by using SDS-PAGE electrophoretic analysis, respectively.

B) Induction of Recombinant Protein Expression

Both transformants were enriched by cultivation in 100 ml LB medium, supplemented with 0.05 mg/ml ampicillin, at 37° C. The induction of heterologous expression of recombinant proteins was initiated by addition of 0.4-1 mM isopropyl-beta-D-thiogalactopyranoside (IPTG; MDBio Inc., Taiwan) and the following incubation at 37° C. for 3 h, when the cell density was approximately 0.4-0.6 at 600 nm.

C) Isolation and Purification of *E. coli* Recombinant Protein rhCRMP-1 and e-rCN3

Cell pellets were harvested by centrifugation, resuspended in PBS buffer and disrupted with glass beads by vortexing for 30 second with 1 min. interval on ice for 15 times. Inclusion bodies were recovered after centrifugation and then resuspended in Buffer B (8M urea, 100 mM Na$_2$HPO$_4$, 10 mM Tris, pH8) for solubilizing the recombinant proteins. The purification of both recombinant proteins was performed by using the His-Bind resin (Ni-NTA His•Bind® Resin, Novagen, USA) and eluted with 50 to 400 mM imidazole elution buffer (8M urea, 100 mM Na$_2$HPO$_4$, 100 mM NaCl, pH8) according to Novagen User Protocol. The presence of recombinant proteins was confirmed by SDS-PAGE and the amino acid sequencing.

The elutes containing expected e-rCN3 protein were pooled, dialyzed against 50 mM Tris-HCl buffer (pH8) to remove urea. The precipitate appearing in the dialyzing solution, which contained e-rCN3 protein, was recovered after centrifugation and resuspended in 100 mM Tris-NaOH buffer (pH 12) with desired concentration.

Example 9

Cytotoxic Effect of Recombinant e-rCN3 Protein

The growth inhibition effect of recombinant e-rCN3 protein was studied with five human cell lines, including the human colon cancer cell line CC-M1, the human breast cancer cell line MCF-7, two human prostate cancer cell lines PC-3 and DU145, and the human prostate epithelium cell line PZ-HPV-7. The e-rCN3 was dissolved in the pH12 Tris-buffer after prepared in diluted cultivation media, as indicated in Example 8, which showed no cytotoxic effect on the testing cell lines. The cytotoxicity assay were performed using MTT method as described by Monks et al. (J. National Cancer Institute 83:757-767 (1991)) or using cell counting-based Hemocytometer method (R. Ian Freshney, WILEY-LISS: 186, 309-312 (2000)) as described in Example 3 and Example 9. Five micromolar (µM) e-rCN3 was applied twice on three prostate cell lines for 6 hours with an interval of 16 hours, while the human colon cancer cell and breast cancer cells were treated with three cycles.

The treatment with 5 µM e-rCN3 achieved over 60% growth inhibition effect on the human colon cell CC-M1 and breast cancer cell MCF-7, while the growth of high-metastatic human prostate cancer cell PC-3 cells was inhibited with approximately 40%. Specifically, no growth inhibition effect on the human prostate epithelium cell line PZ-HPV-7 could be observed after treatment at the same treatment concentrations. It indicates that the cytotoxic effect of e-rCN3 is highly selective and could be applied as therapeutic agent with the expectation of low side effects.

Example 10

Plasmid Construction for Heterologous Expression of CN3 Domain Containing TAT Sequence (e-rTCN3 Fusion Protein)

Protein transduction domains (PTDs) or cell penetrating peptides (CPPs) were first identified while investigating the spontaneous cell entry of HIV transactivator (TAT) protein. TAT protein is involved in the replication of human immunodeficiency virus type I (HIV-1) and able to cross the plasma membrane (Vivès et al., *Journal of Biological Chemistry*, 272:16010-16017 (1997)). Recent works showed that the conjugation of proteins, peptides, and antisense nucleotides to these PTDs could improve the delivery efficacy into the cells (Lindsay, *Current Opinion in Pharmacology*, 2:587-594 (2002)). PTDs are short peptide sequences and the highly cationic 11-amino acid fragment (YGRKKRRQRRR) (SEQ ID NO: 45) of TAT protein has been one of the most well-studied translocating peptides (Albarran et al., *Protein Engineering Design& Selection*, 18: 147-152 (2005)).

An additional translocating peptide of TAT protein fused to CN3 protein at the N-terminal was our strategy to improve the cellular uptake during the in vitro-treatment study and to increase the efficacy of antiproliferation of cancer cells.

A) Construction of Expression Plasmid pETAT

Two oligonucleotides, 5T1 and 3T1R, were mixed at an equal molar ratio, incubated at 94° C. for 5 min, 72° C. for 30 sec, 60° C. for 10 min, and then cooled to room temperature (Arakawa et al., *BMC Biotechnology*, 1:7 (2001)). The annealed short nucleotide fragment was inserted into the Nde I/BamH I site of the pET-22b(+) plasmid (Novagen, USA). This construct was designated as pETAT.

The sequences information of two oligonucleotides are:
(1) 5T1 (SEQ ID NO: 31): 5'-TATGTACGGTCG-TAAAAAACGTCGTCAGCGTCGTCGG-3' (the bold text denotes the coding sequence for transduction domain of HIV TAT protein with a length of 11 amino acids) and
(2) 3T1R (SEQ ID NO: 32): 5'-GATCCCGACGACGCT-GACGACGTTTTTTACGACCGTACA-3' (the bold text denotes the complementary sequence to the oligonucleotide 5T1).

B) Plasmid Construction for Heterologous Expression of e-rTCN3 in *Escherichia coli*

The plasmid pE22bCN3 (Example 7) containing the 850 bp-DNA fragment encoding for the CN3 domain was digested with two restriction endonucleases, Hind III and Xho I, and isolated using agarose gel elution and phenol/isopropanol extraction. This purified 850 bp-DNA fragment was then inserted into the Hind III/Xho I-site of the pETAT plasmid and resulted in the expression plasmid pETAT-CN3.

Example 11

Production of e-rTCN3 Fusion Protein

The expression plasmid pETAT-CN3 was transformed into *Escherichia coli* strain BL21 (DE3). The transformant WJ72-3 (*E. coli* BL21 (DE3)/pETAT-CN3) with the highest production yield at the expected molecular weight (33 kDa) for the fusion protein e-rTCN3 was selected by using SDS-PAGE electrophoretic analysis.

Conditions for cultivation of transformant WJ72-3 and the following induction of over-expression of recombinant e-rTCN3 fusion protein were the same as previously described in Example 8.

The isolation of over-expressed recombinant e-rTCN3 fusion protein was started with preparation of inclusion body fraction (Chang et al., *Protein Engineering*, 15:437-441 (2002)) with modifications. The harvested pellet of *E. coli* transformants was dissolved in the same lysis buffer without lysozyme and disrupted with glass beads by vortexing. The procedures for denaturing and renaturing of e-rTCN3 fusion protein were followed as described by Chang et al. (*Biochemical and Biophysical Research Communications*, 340: 1134-1138 (2006)) with modifications. All of refolding buffers did not contain $Cd^{2+}$ and $Mn^{2+}$ ions. The pH value for the final refolding buffer was ranging from 9 to 10. The e-rTCN3 protein containing solution was finally concentrated using Amicon Ultra (Millipore, USA) centrifugal filters with a molecular weight cut-off of 10 kDa according to the instructions provided by manufacture.

Example 12

Cytotoxic Effect of Recombinant e-rTCN3 Protein

The growth inhibition effect of recombinant e-rTCN3 protein was studied with two human cell lines, human colon cancer cell line CC-M1 and human breast cancer cell line MCF-7. Cell counting-based method using hemocytometer (as described in Example 3) was applied to determine the effect of e-rTCN3 protein on cell proliferation.

The e-rTCN3 protein used for proliferation study was isolated and prepared as described in Example 11.

Two cancer cell lines, CC-M1 and MCF-7, were treated with culture medium containing five micromolar (µM) of recombinant e-rTCN3 protein (treatment medium) at 37° C. for 24 hours, refreshed with new prepared treatment medium and followed with another incubation for 24 hours.

The treatment of recombinant e-rTCN3 protein at the concentration of five-micromolar on the human breast cancer cell line MCF-7 resulted in over 60% growth inhibition, while 40% was resulted for the human colon cancer cell line CC-M1. The recombinant e-rTCN3 protein possessed anti-proliferation effect on cancer cells, specifically, colon cancer cells and breast cancer cells, and it could potentially work as therapeutic agent.

Unless otherwise indicated, all numbers expressing quantities of ingredients, reaction conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

While the invention has been described by way of example and in terms of certain embodiments, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications and patents cited in this disclosure are incorporated by reference in their entirety. To the extent the material incorporated by reference contradicts or is inconsistent with this specification, the specification will supersede any such material. The citation of any references herein is not an admission that such references are prior art to the present invention.

The invention claimed is:

1. An isolated nucleic acid sequence, being selected from the group consisting of SEQ ID NOs: 16, 18, 20, 22, 24, 26, 33, 34, 35, 36, 37, and 38, wherein the isolated nucleic acid sequence encodes a fragment of CRMP-1, in which the fragment is active in inhibiting the proliferation, metastasis, and/or invasion of a cancer cell.

2. An isolated polynucleic acid, which is a polynucleotide fragment of SEQ ID NO: 16 and comprises the nucleotide sequence selected from the group consisting of SEQ ID NOs: 18, 20, 22, 24, 34, 35, 36, and 37, wherein the isolated polynucleic acid encodes an active fragment of CRMP-1.

3. A fusion nucleic acid sequence, consisting of:
    (a) a protein transduction domain (PTD)-coding sequence; and
    (b) an isolated nucleic acid sequence according to claim 1, fused in translation frame to the PTD-coding sequence;
    wherein the active fragment of CRMP-1 encoded thereby has no more than 500 amino acids in length.

4. An isolated nucleic acid sequence, being selected from the group consisting of SEQ ID NOs: 18, 20, 22, 24, 26, 34, 35, 36, 37, and 38, wherein the isolated nucleic acid sequence encodes a fragment of CRMP-1 that is active in inhibiting the proliferation, metastasis, and/or invasion of a cancer cell.

5. A recombinant vector for expression of an active fragment of CRMP-1 comprising:
    (a) at least one regulatory element; and
    (b) an isolated nucleic acid sequence according to claim 1, linked in translation frame to the at least one regulatory element;
    wherein the active fragment of CRMP-1 encoded thereby has no more than 500 amino acids, and wherein the vector does not fully encode SEQ ID NO:1.

6. The recombinant vector of claim 5, wherein the vector is a viral vector.

7. The recombinant vector of claim 5, wherein the vector is selected from the group consisting of an astrovirus, coronavirus, orthomyxovirus, papovavirus, paramyxovirus, parvovirus, picornavirus, poxvirus, or togavirus viral vector.

8. The recombinant vector of claim 5, wherein the at least one regulatory element is a tissue-specific regulatory element.

9. The recombinant vector of claim 5, wherein the isolated nucleic acid sequence is selected from the group consisting of SEQ ID NOs: 18, 20, 22, 24, and 34-37.

10. A recombinant vector for expression of an active fragment of CRMP-1, comprising:
    (a) at least one regulatory element; and
    (b) an isolated nucleic acid sequence according to claim 4, linked in translation frame to the at least one regulatory element;
    wherein the active fragment of CRMP-1 encoded thereby has no more than 500 amino acids, and wherein the vector does not fully encode SEQ ID NO:1.

11. An isolated nucleic acid sequence, which encodes a fragment of CRMP-1, wherein the fragment of CRMP-1 is selected from the group consisting of SEQ ID NOs: 15, 17, 19, 21, 23, 25, and 39-43 and is active in inhibiting the proliferation, metastasis, and/or invasion of a cancer cell, and wherein the nucleic acid has no more than 1500 nucleotides in length.

12. An isolated nucleic acid sequence, which encodes a fragment of CRMP-1, wherein the fragment is selected from the group consisting of SEQ ID NOs: 17, 19, 21, 23, 25 and 39-43 and is active in inhibiting the proliferation, metastasis, and/or invasion of a cancer cell, wherein the isolated nucleic acid sequence is selected from the group consisting of SEQ ID NOs: 18, 20, 22, 24, 26, and 34-38.

13. The isolated nucleic acid sequence of claim 12, wherein the isolated nucleic acid sequence is further selected from the group consisting of SEQ ID NOs: 18, 26, 34 and 38.

14. A recombinant vector for expression of an active fragment of CRMP-1, comprising an isolated nucleic acid sequence according to claim 11, wherein the active fragment of CRMP-1 encoded thereby has no more than 500 amino acids in length, and wherein the vector does not fully encode SEQ ID NO:1.

15. A recombinant vector for expression of an active fragment of CRMP-1 comprising an isolated nucleic acid sequence according to claim 11, wherein the active fragment of CRMP-1 encoded thereby has no more than 500 amino acids in length, and wherein the vector does not fully encode SEQ ID NO:1.

16. A recombinant vector for expression of a fusion protein, comprising:
    (a) a first nucleotide sequence, which encodes an HIV protein transduction domain (PTD); and
    (b) a second nucleotide sequence, which encodes an active fragment of CRMP-1 and is fused in translation frame to the HIV PTD, wherein the active fragment of CRMP-1 is selected from the group consisting of SEQ ID NOs: 15, 17, 19, 21, 23, 25, and 39-43;

and wherein the active fragment of CRMP-1 encoded thereby has no more than 500 amino acids in length, and further wherein the vector does not fully encode SEQ ID NO:1.

17. A recombinant vector for expression of a fusion protein, comprising:
   (a) a first nucleotide sequence, which encodes an HIV protein transduction domain (PTD); and
   (b) a second nucleotide sequence, which encodes an active fragment of CRMP-1 and is fused in translation frame to the HIV PTD, wherein the second nucleotide sequence is selected from the group consisting of SEQ ID NOs: 16, 18, 20, 22, 24, 26, and 33-38;

wherein the active fragment of CRMP-1 encoded thereby has no more than 500 amino acids in length, and wherein the vector does not fully encode SEQ ID NO:1.

18. The recombinant vector of claim 14 further comprising a tissue specific regulatory element linked in frame to the isolated nucleic acid sequence.

* * * * *